United States Patent
Miyawaki et al.

(10) Patent No.: US 10,815,462 B2
(45) Date of Patent: Oct. 27, 2020

(54) MODIFIED LUCIFERASE

(71) Applicant: RIKEN, Saitama (JP)

(72) Inventors: Atsushi Miyawaki, Saitama (JP); Satoshi Iwano, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 16/327,491

(22) PCT Filed: Aug. 25, 2017

(86) PCT No.: PCT/JP2017/030491
§ 371 (c)(1),
(2) Date: Feb. 22, 2019

(87) PCT Pub. No.: WO2018/038248
PCT Pub. Date: Mar. 1, 2018

(65) Prior Publication Data
US 2019/0177704 A1  Jun. 13, 2019

(30) Foreign Application Priority Data
Aug. 25, 2016 (JP) .................. 2016-165053

(51) Int. Cl.
C12N 9/02 (2006.01)
C12N 15/09 (2006.01)
C12Q 1/66 (2006.01)

(52) U.S. Cl.
CPC ........... *C12N 9/0069* (2013.01); *C12N 15/09* (2013.01); *C12Q 1/66* (2013.01); *C12Y 113/12005* (2013.01)

(58) Field of Classification Search
None
See application file for complete search history.

(56) References Cited

U.S. PATENT DOCUMENTS

2008/0226557 A1  9/2008  Miller

FOREIGN PATENT DOCUMENTS

WO  2012-109470 A2  8/2012

OTHER PUBLICATIONS

Viviani et al. (The structural origin and biological function of pH-sensitivity in firefly luciferases, Photochem. Photobiol. Sci., 2008, 7, 159-169).*
Airaksinen et al. (Nucleic Acids Res 26:576-581, 1998).*
Folz et al. (J. Biol. Chem. 263:2070-2078, 1988).*
Accession No. U47295, "Cloning vector pGL3-Basic, complete sequence", Nov. 16, 2005.
International Search Report of PCT/JP2017/030491, dated Nov. 14, 2017.
International preliminary report on patentability of PCT/JP2017/030491, dated Feb. 26, 2019.
EESR in European patent application No. 17843724.0, dated Jan. 8, 2020.
Branchini Bruce R et al: "A Mutagenesis Study of the Putative Luciferin Binding of Firefly Luciferase", Biochemistry 2003, 42, 10429-10436, dated Aug. 13, 2003.
Branchini B R et al: "Red- and green-emitting firefly luciferase mutants for bioluminescent reoprter applications", Analytical Biochemistry 345 (2005) 140-148, dated Oct. 1, 2005.

* cited by examiner

*Primary Examiner* — Suzanne M Noakes
*Assistant Examiner* — Jae W Lee
(74) *Attorney, Agent, or Firm* — Kristina Castellano; Castellano PLLC

(57) ABSTRACT

In order to provide modified luciferase whose substrate specificity to at least one luminescent substrate (e.g., AkaLumine) other than D-luciferin has been improved as compared with to D-luciferin, modified luciferase according to an aspect of the present invention has a mutation at an amino acid corresponding to a 347th amino acid in an amino acid sequence represented by SEQ ID NO: 1.

5 Claims, 1 Drawing Sheet
Specification includes a Sequence Listing.

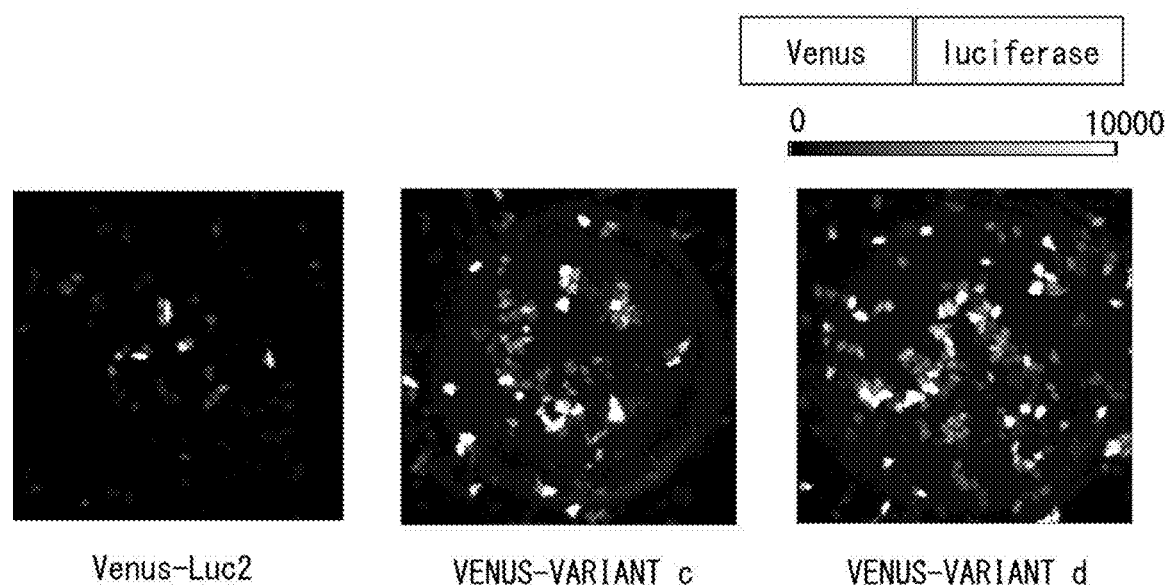

MODIFIED LUCIFERASE

CROSS REFERENCE TO RELATED APPLICATION

This is a U.S. National Stage application of PCT/JP2017/030491 filed on Aug. 25, 2017, which claims priority to Japan Patent Application 2016-165053 filed on Aug. 25, 2016, the contents of both of which are hereby incorporated herein by reference.

TECHNICAL FIELD

The present invention relates to modified luciferase and use of the modified luciferase.

BACKGROUND ART

Light emission from fireflies, widely known as bioluminescence, occurs due to a reaction of a luminescent system of firefly luciferin (D-luciferin)-firefly luciferase. In the luminescent system, a luminescent substrate D-luciferin is converted by firefly luciferase, in the presence of adenosine triphosphate (ATP) and magnesium ions ($Mg^{2+}$), into a luminescent substance oxyluciferin so as to emit light.

It is known that a luminescent system of D-luciferin-luminescent Coleoptera luciferase can be used for analyzing efficiencies of gene expression and gene introduction, monitoring cell proliferation, and the like by introducing a luminescent Coleoptera luciferase gene into a transgene vector or a cell. As such, the luminescent system has been attracting attention and put into practical use in various fields such as life science, biotechnology, medical science, and pharmaceutical science.

In order to apply the luminescent system to various uses, control of light emission is important. The luminescent system will be more useful and easily put to a wider variety of uses if it becomes possible to control emission wavelength, emission behavior, and the like freely. Accordingly, researches have been conducted on substances, other than D-luciferin, which are usable as a luminescent substrate of a luminescent system involving luminescent Coleoptera luciferase.

For example, there have been developed luminescent substrates which have emission wavelengths that are shifted toward a long wavelength side as compared with an emission wavelength of D-luciferin. Patent Literature 1 discloses AkaLumine, which is a compound that emits red-colored light (emission peak: 670 nm to 690 nm).

CITATION LIST

Patent Literature

[Patent Literature 1] Japanese Patent Application Publication, Tokukai, No. 2009-184932 A (Publication Date: Aug. 20, 2009)

SUMMARY OF INVENTION

Technical Problem

Existing known firefly luciferase and similar luciferases maintain high reactivity with D-luciferin. As long as these luciferases are used, it is not possible to construct a luminescent system which specifically reacts with a luminescent substrate (hereinafter generally referred to as "other-color luminescent substrate") having an emission wavelength different from that of D-luciferin. This is a problem arising, for example, in a case of developing a multicolor imaging technique that utilizes two or more kinds of luminescent substrates such as, for example, D-luciferin and an other-color luminescent substrate.

The present invention is accomplished in view of the foregoing problem. An object of the present invention is to provide modified luciferase whose substrate specificity to at least one other-color luminescent substrate (e.g., AkaLumine) other than D-luciferin has been improved as compared with to D-luciferin.

Solution to Problem

In order to attain the object, the present invention provides the following.

1) A polypeptide having a luciferase activity, the polypeptide being defined in any one of (1) through (3) below:

(1) a polypeptide which has (i) a mutation at an amino acid corresponding to a 347th amino acid in an amino acid sequence represented by SEQ ID NO: 1 and (ii) a sequence identity of 85% or more with respect to the amino acid sequence represented by SEQ ID NO: 1; (2) a polypeptide which has (i) a mutation at an amino acid corresponding to the 347th amino acid in the amino acid sequence represented by SEQ ID NO: 1 and (ii) an amino acid sequence which is obtained by substitution, deletion, insertion, and/or addition of 1 to 82 amino acids with respect to the amino acid sequence represented by SEQ ID NO: 1; and (3) a polypeptide which is encoded by a polynucleotide that hybridizes under stringent conditions with a polynucleotide consisting of a sequence complementary to a polynucleotide that encodes a polypeptide having the amino acid sequence represented by SEQ ID NO: 1 and which has a mutation at an amino acid corresponding to the 347th amino acid in the amino acid sequence represented by SEQ ID NO: 1.

2) A nucleic acid including a base sequence encoding a polypeptide as set forth in 1).

3) A vector including a nucleic acid as set forth in 2). 4) A kit including a nucleic acid as set forth in 2) or a vector as set forth in 3).

5) A method for detecting light emission, comprising the step of: reacting a polypeptide as set forth in 1) with at least one luminescent substrate other than D-luciferin.

6) A method for designing modified luciferase whose substrate specificity to at least one luminescent substrate other than D-luciferin has been improved as compared with to D-luciferin, the method comprising the step of: causing a mutation at an amino acid in luciferase, the amino acid corresponding to a 347th amino acid in an amino acid sequence represented by SEQ ID NO: 1.

Advantageous Effects of Invention

The present invention allows providing modified luciferase whose substrate specificity to at least one other-color luminescent substrate (e.g., AkaLumine) has been improved as compared with to D-luciferin.

BRIEF DESCRIPTION OF DRAWINGS

FIG. 1 is a view showing results of fluorescence observation in an Example of the present invention.

DESCRIPTION OF EMBODIMENTS

The description below deals with an embodiment of the present invention in detail.

Definitions of Terms and the Like

In the present specification, the term "polynucleotide" is interchangeable with "nucleic acid" or "nucleic acid molecule". The term "polynucleotide", unless otherwise specified, includes in its scope a polynucleotide that contains an already known analog of a naturally-existing nucleotide having a function as well as the naturally-existing nucleotide. The term "base sequence" is interchangeable with "nucleic acid sequence" or "nucleotide sequence", and intends to refer to a deoxyribonucleotide sequence or a ribonucleotide sequence unless otherwise indicated. The polynucleotide may have a single-stranded structure or a double-stranded structure, and may be a sense strand or an antisense strand in the case of a single strand.

In the present specification, the term "gene" refers to a "polynucleotide" that encodes a protein.

In the present specification, an "expression regulatory region" of a gene refers to a "polynucleotide" that regulates expression of the gene. Examples of the "expression regulatory region" include a promoter region and an enhancer region.

In the present specification, the term "expression cassette" refers to an expression unit including (i) a functional expression regulatory region in a host to be expressed and (ii) a polynucleotide operably linked to the expression regulatory region. In the expression cassette, the polynucleotide is preferably a gene or a gene fragment. An example of the expression cassette is an expression unit in which the above expression regulatory region is linked to the above polynucleotide in a genetically engineered manner. The term "operably linked" refers to a state in which expression of a polynucleotide is controlled with use of an expression regulatory sequence. The expression cassette may be in the form of an expression vector.

In the present specification, the term "polypeptide" is interchangeable with "protein". A "polypeptide" includes a structure of amino acids linked by a peptide bond. A "polypeptide" may further include a structure of a sugar chain or an isoprenoid group and the like. The term "polypeptide", unless otherwise specified, includes in its scope a polypeptide that contains an already known analog of a naturally-existing amino acid having a function as well as the naturally-existing amino acid.

In the present specification, the terms "luminescent polypeptide", "polypeptide having a luciferase activity", and "luciferase" refer to a polypeptide having a property of an enzyme having an activity of catalyzing a chemical reaction (luminescent reaction) in which a luminescent substrate emits light.

In the present specification, the expression "A and/or B" is a concept covering both "A and B" and "A or B", and is interchangeable with "at least one of A and B".

In the present specification, the term "luminescent substrate" refers to a substrate which exhibits a luminescent phenomenon through an enzymatic reaction by a luminescent polypeptide. A color of light emitted in a luminescent reaction depends on a luminescent substrate. Accordingly, in the present invention, the term "other-color luminescent substrate" refers to a luminescent substrate having an emission peak different from that (approximately 560 nm) of D-luciferin.

In the present specification, the term "an amino acid corresponding to a Y-th amino acid in an amino acid sequence represented by SEQ ID NO: X" refers to an amino acid which is identified by homology analysis as corresponding to the Y-th position in the amino acid sequence represented by SEQ ID NO: X. Note that the homology analysis is performed by a method using pairwise sequence alignment such as Needleman-Wunsch method and Smith-Waterman method, or a method using multiple sequence alignment such as ClustalW method. On the basis of these methods, a person skilled in the art will be able to understand "a corresponding amino acid" in an amino acid sequence to be analyzed, by using an amino acid sequence represented by SEQ ID NO: X as a reference sequence. Examples of the amino acid sequence to be analyzed include an isoform, homologue, or mutant of the reference sequence. The analysis may be conducted with use of a default setting, or with use of a setting in which parameters have been appropriately changed from the default setting as necessary.

In the present specification, amino acid "mutation" refers to substitution, deletion, or insertion of amino acids. In the present invention, mutation is preferably substitution or deletion, more preferably substitution.

[1. Luminescent Polypeptide]

A polypeptide of the present invention is modified luciferase having a mutation at an amino acid corresponding to a 347th amino acid in an amino acid sequence represented by SEQ ID NO: 1, and is a luminescent polypeptide having a characteristic amino acid sequence of any one of the following (1) through (3). A polypeptide of the present invention may hereinafter be referred to as a modified luciferase of the present invention or as a luminescent polypeptide of the present invention.

(1) A luminescent polypeptide having a sequence identity of 85% or more with respect to the amino acid sequence represented by SEQ ID NO: 1. The sequence identity is preferably 90% or more, more preferably 95% or more, particularly preferably 96% or more, 97% or more, 98% or more, or 99% or more.

(2) A luminescent polypeptide having an amino acid sequence which is obtained by substitution, deletion, insertion, and/or addition of 1 to 82 amino acids with respect to the amino acid sequence represented by SEQ ID NO: 1. The number of amino acids that have been substituted, deleted, inserted, and/or added is preferably 1 to 55, more preferably 1 to 28, even more preferably 1 to 22, particularly preferably 1 to 17, 1 to 11, or 1 to 5.

(3) A polypeptide which is encoded by a polynucleotide that hybridizes under stringent conditions with a polynucleotide consisting of a sequence complementary to a polynucleotide that encodes a polypeptide having the amino acid sequence represented by SEQ ID NO: 1 and which has a mutation at an amino acid corresponding to the 347th amino acid in the amino acid sequence represented by SEQ ID NO: 1. The stringent condition will be described in a later section of a polynucleotide according to the present invention.

The origin of modified luciferase of the present invention is not particularly limited as long as it is luciferase having an amino acid corresponding to the 347th amino acid in the amino acid sequence represented by SEQ ID NO: 1, and can be, for example, luciferase of an organism belonging to the order Coleoptera or the like. Examples of the organism belonging to the order Coleoptera include an organism belonging to the family Lampyridae and an organism belonging to the family Omethidae (note that SEQ ID NO: 1 is an amino acid sequence of luciferase derived from *Photinus pyralis*). Examples of the organism belonging to the family Lampyridae include an organism belonging to the genus *Photinus* and an organism belonging to the genus *Luciola*. Examples of the organism belonging to the genus *Photinus* include *Photinus pyralis*. Examples of the organism belonging to the genus *Luciola* include *Luciola cruciata, Luciola lateralis*, and *Luciola italica*. Examples of the organism belonging to the family Omethidae include an organism belonging to the genus *Phrixothrix*. Examples of the organism belonging to the genus *Phrixothrix* include *Phrixothrix hirtus*. Note that an amino acid sequence of wild-type luciferase in each of these organisms is easily available from a public database such as GenBank, for example.

For example, a 349th amino acid (serine) in wild-type luciferase (GenBank Accession No. M26194) of *Luciola cruciata* and a 349th amino acid (serine) in wild-type luciferase (GenBank Accession No. X66919) of *Luciola lateralis* correspond to the 347th amino acid (serine) in SEQ ID NO: 1.

In modified luciferase of the present invention, a mutated amino acid which is an amino acid introduced in place of an amino acid corresponding to the 347th amino acid is not limited to a specific kind, and can be substituted by any amino acid. The mutated amino acid may be a natural amino acid or a non-natural amino acid, but in an example, the mutated amino acid is preferably a natural amino acid. The mutated amino acid may be an amino acid which, in terms of all of electric charge, polarity, and bulkiness, resembles an unmutated amino acid which is the original amino acid that has not gone through mutation, or may be an amino acid which does not resemble the unmutated amino acid in at least one of electric charge, polarity, and bulkiness.

Preferable examples of the mutated amino acid include cysteine, methionine, alanine, glycine, valine, isoleucine, leucine, phenylalanine, tyrosine, tryptophan, asparagine, threonine, glutamine, and proline. More preferable examples of the mutated amino acid include cysteine, methionine, alanine, glycine, valine, asparagine, threonine, and glutamine. Even more preferable examples of the mutated amino acid include cysteine and asparagine. Particularly preferable examples of the mutated amino acid include asparagine.

Modified luciferase according to an embodiment of the present invention, as compared with the luciferase (e.g., luc2) in which the amino acid corresponding to the 347th amino acid has not been mutated, has a significantly lower reactivity with D-luciferin while maintaining an equivalent reactivity to or having an improved reactivity to an other-color luminescent substrate. Accordingly, the modified luciferase has a relatively increased substrate specificity to the other-color luminescent substrate. Examples of the "other-color luminescent substrate" include a compound (AkaLumine or the like) having a similar structure to luciferin (described in Japanese Patent Application Publication Tokukai No. 2009-184932), a luciferin analog (described in Japanese Patent Application Publication Tokukai No. 2010-215795), and analogs thereof.

In an embodiment, modified luciferase of the present invention, as compared with luciferase (e.g., luc2) in which an amino acid corresponding to the 347th amino acid has not been mutated, has at least an improved substrate specificity to AkaLumine. In another embodiment, the modified luciferase, as compared with luciferase (e.g., luc2) in which an amino acid corresponding to the 347th amino acid has not been mutated, has at least an improved substrate specificity to AkaLumine and an improved substrate specificity to 6-AkaLumine. In another embodiment, the modified luciferase, as compared with the luciferase (e.g., luc2) in which an amino acid corresponding to the 347th amino acid has not been mutated, has at least an improved substrate specificity to AkaLumine, an improved substrate specificity to 6-AkaLumine, and an improved substrate specificity to monoene NMe2.

In an embodiment, modified luciferase of the present invention has a higher substrate specificity to an other-color luminescent substrate than to D-luciferin in that relative comparison of emission intensities shows that an emission intensity with the other-color luminescent substrate is higher than that with D-luciferin. The other-color luminescent substrate, for example, is at least one selected from the group consisting of AkaLumine, 6-AkaLumine, and monoene NMe2.

The substrate specificity of luciferase can be evaluated, for example, by (i) reacting the luciferase of interest with a specific luminescent substrate while conducting emission intensity measurement for one minute to obtain, as a reference, an integrated value of emission intensities thus measured and (ii) comparing the reference with an integrated value which has been obtained by similarly reacting the luciferase of interest with an other-color luminescent substrate. Whether or not the modified luciferase has an improved substrate specificity to at least one other-color luminescent substrate as compared with unmuted luciferase can be confirmed by making a comparison between the substrate specificity, calculated in the above-described manner, of the modified luciferase and the substrate specificity of the unmutated luciferase (for details, see later described Examples as well).

A method for evaluating a substrate specificity of modified luciferase of the present invention is specifically illustrated below.

In one aspect of evaluation, modified luciferase of the present invention is reacted with D-luciferin, and emission intensity measurement is conducted for one minute to obtain an integrated value of emission intensities measured. The integrated value is used as a reference value. The modified luciferase of the present invention is reacted with AkaLumine, and emission intensity measurement is conducted for one minute to obtain an integrated value of emission intensities measured. Then, the integrated value is converted into a relative value on the basis of the reference value. Note here that the relative value of the substrate specificity of the modified luciferase of the present invention to AkaLumine, in comparison with a substrate specificity to D-luciferin, is 2 or more, preferably 4 or more, more preferably 10 or more, even more preferably 20 or more.

In another embodiment, luc2 (luciferase derived from *Photinus pyralis*) consisting of the amino acid sequence represented by SEQ ID NO: 1 is reacted with AkaLumine, and emission intensity measurement is conducted for one minute to obtain an integrated value of emission intensities measured. The integrated value is used as a reference value. The modified luciferase of the present invention is reacted with AkaLumine, and emission intensity measurement is conducted for one minute to obtain an integrated value of emission intensities measured. Then, the integrated value is converted into a relative value on the basis of the reference value. Note here that the relative value of the modified luciferase of the present invention to AkaLumine is 0.8 or more, preferably 2 or more, more preferably 3 or more, even more preferably 6 or more.

In another embodiment, luc2 consisting of the amino acid sequence represented by SEQ ID NO: 1 is reacted with D-luciferin, and emission intensity measurement is conducted for one minute to obtain an integrated value of emission intensities measured. The integrated value is used as a reference value. The modified luciferase of the present invention is reacted with D-luciferin, and emission intensity measurement is conducted for one minute to obtain an integrated value of emission intensities measured. Then, the integrated value is converted into a relative value on the basis of the reference value. Note here that the relative value of the modified luciferase of the present invention to D-luciferin is 0.05 or less, preferably 0.01 or less, more preferably 0.001 or less.

In another embodiment, luc2 consisting of the amino acid sequence represented by SEQ ID NO: 1 is reacted with AkaLumine, and emission intensity measurement is conducted for one minute to obtain an integrated value of emission intensities measured. The integrated value is used as a reference value. The modified luciferase of the present invention is reacted with AkaLumine, and emission intensity measurement is conducted for one minute to obtain an integrated value of emission intensities measured. Then, the integrated value is converted into a relative value on the basis of the reference value. Similarly, luc2 or the modified luciferase of the present invention is reacted with D-luciferin, and emission intensity measurement is conducted for one minute to obtain an integrated value of emission intensities measured. Then, the integrated value is converted into a relative value on the basis of the reference value. With use of the relative values thus obtained, a value of each luciferase with respect to AkaLumine is normalized with use of a value of the each luciferase with respect to D-luciferin so as to obtain a ratio between reactivity to AkaLumine and reactivity to D-luciferin. Note here that a ratio between reactivity to AkaLumine and reactivity to D-luciferin of the modified luciferase of the present invention is higher than that of luc2 by 100 times or more, preferably 200 times or more, more preferably 300 times or more.

In an embodiment, the modified luciferase may further have a mutation at an amino acid which is located at a position other than that of the amino acid corresponding to a 347th amino acid in the amino acid sequence represented by SEQ ID NO: 1.

For example, the modified luciferase may be obtained by expressing a mutant in which a mutation is artificially introduced by a site-directed mutagenesis method into a polynucleotide encoding a luminescent polypeptide having a mutation at an amino acid corresponding to the 347th amino acid in the amino acid sequence represented by SEQ ID NO: 1. Examples of the site-directed mutagenesis method include a Kunkel method (Kunkel et al. (1985): Proc. Natl. Acad. Sci. USA, vol. 82, p. 488-). Note that a similar site-directed mutagenesis method may be used also in a case of introducing a mutation at an amino acid corresponding to the 347th amino acid in the amino acid sequence represented by SEQ ID NO: 1.

As for a region suitable for introducing amino acid mutation for the modified luciferase of the present invention, for example, regions in SEQ ID NO: 1 such as an amino acid corresponding to threonine at position 39 (e.g., substitution to alanine), an amino acid corresponding to glutamic acid at position 48 (e.g., substitution to glutamine), an amino acid corresponding to isoleucine at position 51 (e.g., substitution to valine), an amino acid corresponding to lysine at position (e.g., substitution to arginine), an amino acid corresponding to leucine at position 86 (e.g., substitution to serine), an amino acid corresponding to glutamine at position 134 (e.g., substitution to arginine), an amino acid corresponding to isoleucine at position 136 (e.g., substitution to valine), an amino acid corresponding to asparagine at position 138 (e.g., substitution to aspartic acid), an amino acid corresponding to glutamine at position 147 (e.g., substitution to arginine), an amino acid corresponding to threonine at position 169 (e.g., substitution to alanine), an amino acid corresponding to glycine at position 175 (e.g., substitution to serine), an amino acid corresponding to serine at position 185 (e.g., substitution to cysteine), an amino acid corresponding to asparagine at position 229, an amino acid corresponding to isoleucine at position 231 (e.g., substitution to asparagine), an amino acid corresponding to leucine at position 264 (e.g., substitution to phenylalanine), an amino acid corresponding to threonine at position 290 (e.g., substitution to alanine), an amino acid corresponding to leucine at position 291 (e.g., substitution to proline), an amino acid corresponding to phenylalanine at position 294 (e.g., substitution to cysteine), an amino acid corresponding to phenylalanine at position 295 (e.g., substitution to leucine), an amino acid corresponding to asparagine at position 308 (e.g., substitution to serine), an amino acid corresponding to histidine at position 310 (e.g., substitution to arginine), an amino acid corresponding to histidine at position 332 (e.g., substitution to arginine), an amino acid corresponding to isoleucine at position 349 (e.g., substitution to valine), an amino acid corresponding to leucine at position 350 (e.g., substitution to methionine), an amino acid corresponding to aspartic acid at position 357 (e.g., substitution to arginine), an amino acid corresponding to alanine at position 361 (e.g., substitution to serine), an amino acid corresponding to histidine at position 377 (e.g., substitution to valine), an amino acid corresponding to serine at position 456 (e.g., substitution to glycine), an amino acid corresponding to asparagine at position 463 (e.g., substitution to tyrosine), an amino acid corresponding to lysine at position 524 (e.g., substitution to arginine), an amino acid corresponding to leucine at position 526 (e.g., substitution to proline or serine), an amino acid corresponding to isoleucine at position 540 (e.g., substitution to threonine), and an amino acid corresponding to glycine at position 545 (e.g., substitution to aspartic acid) are more suitable for introducing amino acid mutation.

As an example of more preferable mutation, the modified luciferase of the present invention further has a mutation at an amino acid corresponding to the 229th amino acid in the amino acid sequence represented by SEQ ID NO: 1.

For example, a 231st amino acid (asparagine) in wild-type luciferase of Luciola cruciata and a 231st amino acid (asparagine) in wild-type luciferase of Luciola lateralis correspond to the 229th amino acid (asparagine) in SEQ ID NO: 1.

A mutated amino acid which is an amino acid introduced in place of an amino acid corresponding to the 229th amino acid is not limited to a specific kind, and can be substituted by any amino acid. The mutated amino acid may be a natural amino acid or a non-natural amino acid. In an example, the mutated amino acid is preferably a natural amino acid. The mutated amino acid may be an amino acid which, in terms of all of electric charge, polarity, and bulkiness, resembles an unmutated amino acid which is the original amino acid that has not gone through mutation, or may be an amino acid which does not resemble the unmutated amino acid in at least one of electric charge, polarity, and bulkiness.

In a case where the amino acid corresponding to the 229th amino acid is asparagine, examples of the mutated amino acid include glycine, alanine, valine, leucine, isoleucine, serine, threonine, cysteine, methionine, phenylalanine, tryptophan, tyrosine, proline, glutamine, glutamic acid, aspartic acid, lysine, arginine, and histidine. Examples of an amino acid resembling asparagine in electric charge include glycine, alanine, valine, leucine, isoleucine, serine, threonine, cysteine, methionine, phenylalanine, tryptophan, tyrosine, proline, and glutamine. Examples of an amino acid resembling asparagine in polarity include glycine, serine, threonine, cysteine, tyrosine, proline, glutamine, glutamic acid, aspartic acid, lysine, arginine, and histidine. Examples of an amino acid resembling asparagine in bulkiness include threonine and glutamine.

Preferable examples of the mutated amino acid which is an amino acid introduced in place of the amino acid corresponding to the 229th amino acid include tyrosine, phenylalanine, tryptophan, histidine, arginine, and lysine. More preferable examples of the mutated amino acid include tyrosine and histidine. Particularly preferable examples of the mutated amino acid include tyrosine.

A combination of a mutated amino acid which is an amino acid introduced in place of the amino acid corresponding to the 347th amino acid and a mutated amino acid which is an amino acid introduced in place of the amino acid corresponding to the 229th amino acid is not particularly limited. In an embodiment, preferable examples of the combination include the following.

Position corresponding to the 347th amino acid: cysteine, position corresponding to the 229th amino acid: tyrosine Position corresponding to the 347th amino acid: cysteine, position corresponding to the 229th amino acid: histidine Position corresponding to the 347th amino acid: asparagine, position corresponding to the 229th amino acid: tyrosine Position corresponding to the 347th amino acid: asparagine, position corresponding to the 229th amino acid: histidine In another example, it is preferable that the modified luciferase of the present invention further have a mutation at an amino acid corresponding to the 310th amino acid in the amino acid sequence represented by SEQ ID NO: 1.

For example, a 312nd amino acid (valine) in wild-type luciferase of Luciola cruciata and a 312nd amino acid (valine) in wild-type luciferase of Luciola lateralis correspond to the 310th amino acid (histidine) in SEQ ID NO: 1.

A mutated amino acid which is an amino acid introduced in place of the amino acid corresponding to the 310th amino acid is not limited to a specific kind, and can be substituted by any amino acid. The mutated amino acid may be a natural amino acid or a non-natural amino acid. In an example, the mutated amino acid is preferably a natural amino acid. The mutated amino acid may be an amino acid which, in terms of all of electric charge, polarity, and bulkiness, resembles an unmutated amino acid which is the original amino acid that has not gone through mutation, or may be an amino acid which does not resemble the unmutated amino acid in at least one of electric charge, polarity, and bulkiness.

In a case where the amino acid corresponding to the 310th amino acid is histidine, examples of the mutated amino acid include glycine, alanine, valine, leucine, isoleucine, serine, threonine, cysteine, methionine, phenylalanine, tryptophan, tyrosine, proline, glutamine, asparagine, glutamic acid, aspartic acid, lysine, and arginine. Examples of an amino acid resembling histidine in electric charge include lysine and arginine. Examples of an amino acid resembling histidine in polarity include glycine, serine, threonine, cysteine, tyrosine, proline, glutamine, asparagine, glutamic acid, aspartic acid, lysine, and arginine.

Preferable examples of a mutated amino acid which is an amino acid introduced in place of the amino acid corresponding to the 310th amino acid has been mutated include glutamine, asparagine, threonine, arginine, histidine, and lysine. More preferable examples of the mutated amino acid include glutamine and arginine.

More preferable examples of a combination of a mutated amino acid which is an amino acid introduced in place of the amino acid corresponding to the 347th amino acid has been mutated, a mutated amino acid into which the amino acid corresponding to the 229th amino acid has been mutated, and a mutated amino acid into which the amino acid corresponding to the 310th amino acid has been mutated include the following.

Position corresponding to the 347th amino acid: cysteine, position corresponding to the 229th amino acid: tyrosine, position corresponding to amino acid 310: glutamine Position corresponding to the 347th amino acid: asparagine, position corresponding to the 229th amino acid: tyrosine, position corresponding to amino acid 310: glutamine A luminescent polypeptide according to the present invention may be chemically synthesized. More specifically, the fluorescent polypeptide includes in its scope a product of chemical synthesis procedure, and a translated product obtained from a procaryotic host or a eucaryotic host (e.g., bacterial cell, yeast cell, higher plant cell, insect cell, or mammalian cell) by a recombination technique.

In an embodiment, the modified luciferase may be a fusion polypeptide having an additional amino acid sequence at N-terminus and/or C-terminus. The additional amino acid sequence may have or not have a specific function. Examples of the fusion polypeptide include a fusion protein produced by expression of an expression cassette and/or vector according to the present invention; a fusion protein in which a protein is labeled with a luminescent polypeptide according to the present invention; a fusion protein produced by fusing a luminescent polypeptide in accordance with the present invention with a predetermined peptide sequence for stabilizing light emission; and a BRET probe containing a luminescent polypeptide according to the present invention and another fluorescent polypeptide. In other words, the kind of another polypeptide to be fused with a luminescent polypeptide according to the present invention is not particularly limited. A fusion polypeptide according to the present invention may be chemically synthesized or produced with use of a gene recombination technique by a method similar to the method for producing a luminescent polypeptide according to the present invention.

In an embodiment, examples of modified luciferase which is preferable in terms of having an improved substrate specificity to at least one other-color luminescent substrate include modified luciferase including or consisting of an amino acid sequence having a sequence identity of 70% or more, 75% or more, 80% or more, 85% or more, 90% or more, 95% or more, 98% or more, or 100% with respect to an amino acid sequence represented by any one of SEQ ID NOS: 2 through 7. It is preferable that this modified luciferase maintains all of amino acid mutations corresponding to amino acid mutations included in the amino acid sequence of any one of SEQ ID NOS: 2 through 7. An amino acid mutation included in the amino acid sequence of any one of SEQ ID NOS: 2 through 7 means a mutation in comparison with the amino acid sequence represented by SEQ ID NO: 1.

[2. Polynucleotide Encoding Luminescent Polypeptide]

A polynucleotide according to the present invention encodes any one of the above luminescent polypeptides. The polynucleotide is specifically a polynucleotide defined in any one of (1-1) to (1-3) below.

(1-1) A polynucleotide encoding a luminescent polypeptide which has (i) a mutation at an amino acid corresponding to a 347th amino acid in an amino acid sequence represented by SEQ ID NO: 1 and (ii) a sequence identity of 85% or more with respect to the amino acid sequence represented by SEQ ID NO: 1. The sequence identity of the amino acid sequence is preferably 90% or more, more preferably 95% or more, particularly preferably 96% or more, 97% or more, 98% or more, or 99% or more.

(1-2) A polynucleotide encoding a luminescent polypeptide having an amino acid sequence which is obtained by substitution, deletion, insertion, and/or addition of 1 to 82 amino acids with respect to the amino acid sequence represented by SEQ ID NO: 1. The number of amino acids that have been substituted, deleted, inserted, and/or added is preferably 1 to 55, more preferably 1 to 28, even more preferably 1 to 22, particularly preferably 1 to 17, 1 to 11, or 1 to 5.

(1-3) A polynucleotide which hybridizes under stringent conditions with a polynucleotide consisting of a sequence complementary to a polynucleotide that encodes the amino acid sequence represented by SEQ ID NO: 1, an amino acid sequence encoded by the polynucleotide having a mutation at an amino acid corresponding to the 347th amino acid in the amino acid sequence represented by SEQ ID NO: 1.

The stringent conditions are, for example, conditions described in the reference document "Molecular cloning—a Laboratory manual 2nd edition" (Sambrook et al., 1989). Specifically, the stringent conditions are, for example, (i) conditions that hybridization is conducted by incubating at 65° C. for 8 to 16 hours together with a probe, in a solution that contains 6×SSC (composition of 1×SSC: 0.15 M of sodium chloride, 0.015 M of sodium citrate, pH 7.0), 0.5% of SDS, 5×Denhardt's solution, and 100 mg/mL of herring sperm DNA and (ii) conditions that, after hybridization is carried out under the above conditions, washing is conducted at 65° C. in a solution containing salt at a concentration of approximately 0.1 M or lower, preferably in 0.2×SSC or any other solution having an ionic strength equivalent thereto. The polynucleotide has a sequence identity of preferably 85% or more, more preferably 90% or more, even more preferably 95% or more, 96% or more, 97% or more, 98% or more, or 99% or more with respect to the base sequence of the polynucleotide in (1-1).

Introduction of a mutation into a base sequence is performed as described above in the section [1. Luminescent Polypeptide]. An example of a base sequence of a DNA encoding luciferase represented by SEQ ID NO: 1 is a base sequence represented by SEQ ID NO: 8. Accordingly, for example, by introducing a mutation into the base sequence represented by SEQ ID NO: 8, a nucleic acid including a base sequence encoding modified luciferase can be easily obtained.

A polynucleotide according to the present invention may be present in the form of an RNA (e.g., mRNA) or a DNA (e.g., cDNA or genomic DNA). The DNA may be double-stranded or single-stranded. A polynucleotide according to the present invention may have an additional sequence such as a sequence of an untranslated region (UTR).

A polynucleotide according to the present invention may be produced by, for example, a method that involves amplification means such as PCR. An example method involves (i) preparing a primer from each of a 5' side and a 3' side of the sequence (or complementary sequences thereof) of cDNA of the polynucleotide, (ii) performing, for example, PCR by using the above primers with genomic DNA (cDNA) or the like as a template, and (iii) amplifying the DNA region between the two primers. This method allows a DNA fragment containing a polynucleotide according to the present invention to be produced in a large amount.

[3. Vector, Expression Cassette]

A polynucleotide according to the present invention (for example, DNA) may be inserted in an appropriate vector for use in the form of a vector. The vector may be of a kind such that the vector replicates itself autonomously as with a plasmid or that the vector is, when introduced into a host cell, integrated with a genome of the host cell and is replicated together with a chromosome of the host cell.

The above vector is preferably an expression vector. In the expression vector, a polynucleotide according to the present invention is functionally linked to, for example, elements necessary for transcription (such as a promoter sequence) that are functionally linked to each other. A promoter sequence is a DNA sequence that exhibits transcriptional activity in a host cell. The kind of the promoter sequence to be used may be selected as appropriate depending on the kind of the host cell and the purpose of using a luminescent polypeptide according to the present invention. Example kinds of the host cell include those described under [4. Transformant and Method for Producing Transformant].

A promoter sequence operable in a host cell is, for example, a promoter of *Bacillus stearothermophilus* maltogenic amylase gene, *Bacillus licheniformis* alpha-amylase gene, *Bacillus amyloliquefaciens* BAN amylase gene, *Bacillus Subtilis* alkaline protease gene, or *Bacillus pumilus* xylosidase gene; a PR promoter or PL promoter of phage lambda; lac promoter, trp promoter, or tac promoter of *Escherichia coli*; or polyhedrin promoter, P10 promoter, *Autographa californica* polyhedrosis basic protein promoter, baculovirus immediate-type early gene 1 promoter, baculovirus 39K delayed-type early gene promoter, a promoter derived from yeast glycolysis gene, alcohol dehydrogenase gene promoter, TPI1 promoter, ADH2-4c promoter, ADH3 promoter, tpiA promoter, 35S promoter of cauliflower mosaic virus, SV40 promoter, MT-1 (metallothionein gene) promoter, cytomegalo promoter, or adenovirus 2 major late promoter.

In an expression vector, the polynucleotide in accordance with the present invention may be functionally bonded as necessary to an appropriate terminator (for example, polyadenylation signal, growth hormone terminator of a mammal, TPI1 terminator, or ADH3 terminator). The kind of the appropriate terminator may be selected as appropriate depending on the kind of the host cell.

A vector according to the present invention may further include an element such as a transcription enhancer sequence or translation enhancer sequence.

A vector according to the present invention may further have a DNA sequence that allows the vector to be replicated in the host cell. In a case where the host cell is a mammalian cell, the DNA sequence is, for example, an SV40 replication origin.

A vector according to the present invention may further have a selective marker. The selective marker is, for example, a drug resistance gene against a drug such as ampicillin, kanamycin, tetracycline, chloramphenicol, neomycin, or hygromycin.

An expression cassette according to the present invention is an expression cassette including (a) an expression regulatory region functional in an expression host and (b) a polynucleotide according to the present invention. An expression cassette according to the present invention may be in the form of the expression vector described above.

[4. Transformant and Method for Producing Transformant]

(Transformant and Method for Producing Transformant) Introducing a polynucleotide according to the present invention, an expression cassette according to the present invention, or a vector according to the present invention into an appropriate host cell allows for establishment of a transformant. The transformant contains the full length of a polynucleotide according to the present invention or at least part of the polynucleotide, and allows for expression of any one of the luminescent polypeptides of the present invention. Similarly, progeny of a transformant according to the present invention obtained by the use of the transformant also contains the full length of a polynucleotide according to the present invention or at least part of the polynucleotide, and allows for expression of any one of the luminescent polypeptides of the present invention. In the transformant or its progeny, the full length of a polynucleotide according to the present invention or part of the polynucleotide is preferably integrated in a genome.

The description below uses the term "exogenous (foreign) nucleic acid molecule" of the present invention to collectively refer to a polynucleotide according to the present invention, an expression cassette according to the present invention, and a vector according to the present invention. The method for introducing an exogenous nucleic acid molecule of the present invention into a host cell may be selected depending on the kind of the host cell as described later as an example. Further, the method for obtaining progeny of a transformant according to the present invention may be selected depending on the kind of the transformant.

Examples of the host cell include a bacterial cell, a yeast cell, a fungal cell other than a yeast cell, and a higher eukaryotic cell. Examples of the higher eukaryotic cell include a plant cell and an animal cell. Examples of the animal cell include an insect cell, an amphibian cell, a reptile cell, an avian cell, a fish cell, and a mammalian cell. Examples of the bacterial cell include a Gram-positive bacterium such as *Bacillus* and *Streptomyces*; and a Gram-negative bacterium such as *Escherichia coli*. The yeast cell is, for example, a cell belonging to *Saccharomyces* or *Schizosaccharomyces*, and specific examples include *Saccharomyces cerevisiae* and *Saccharomyces kluyveri*. The fungal cell other than a yeast cell is, for example, a filamentous fungus cell. Examples of the filamentous fungus cell include a filamentous fungus cell belonging to *Aspergillus, Neurospora, Fusarium,* or *Trichoderma*. Examples of the insect cell include a silkworm cell. The mammalian cell is, for example, HEK293 cell, HeLa cell, COS cell, BHK cell, CHL cell, or CHO cell.

The method for transformation of a host cell may be selected as appropriate depending on, for example, the kind of the host cell. Examples of the method include protoplast method, method involving use of a competent cell, electroporation method, spheroplast method, acetic acid lithium method, calcium phosphate method, lipofection method, *Agrobacterium* method, and particle gun method. Another method for transformation of a host cell is, for example, a method for performing transformation by producing a host cell in which an exogenous nucleic acid molecule of the present invention has been integrated in a host chromosome. The integration of an exogenous nucleic acid molecule into a host chromosome can be performed by, for example, homologous recombination or heterologous recombination. Still another method for transformation of a host cell is, for example, a method of (i) cotransforming an exogenous nucleic acid molecule of the present invention and a baculovirus into a host cell to produce a recombinant baculovirus in a supernatant of the host cell culture and then (ii) infecting the host cell with the recombinant baculovirus to cause the host cell to produce a luminescent polypeptide according to the present invention. Example methods of the cotransfection include calcium phosphate method and lipofection method.

The transformant is cultured or cultivated under a condition that allows the introduced exogenous nucleic acid molecule to be expressed.

The form of the transformant is not limited to a cell: The transformant may be, for example, tissue, organ, or individual that has been transformed with use of an exogenous nucleic acid molecule according to the present invention. A transformant other than a cell may preferably be of a non-human origin, and is preferably of a non-human origin particularly in a case where the transformant is an individual. The description below uses the term "non-human transgenic organism" to refer to a transformed individual of a non-human origin.

(Non-Human Transgenic Organism and Method for Production Thereof)

A non-human transgenic organism according to the present invention is, for example, a higher organism. Example transgenic plants include transgenic forms of dicotyledons such as *Arabidopsis thaliana*; and monocotyledons such as *Brachypodium distachyon*, rice, wheat, and barley. Example transgenic animals include transgenic forms of animals such as zebrafish, mouse, rat, and pig.

The method for producing a non-human transgenic organism according to the present invention may simply be selected depending on the kind of the transgenic organism. Example methods for producing a transgenic animal include (i) a method of, on the basis of microinjection method or the like, introducing an exogenous nucleic acid molecule according to the present invention in vitro into a fertilized egg collected from a donor organism and (ii) a method of infecting in vitro a cell of an early developed germ derived from a donor organism with a viral vector such as a retrovirus. A transgenic plant may simply be produced by a method of, for example, (i) introducing an exogenous nucleic acid molecule according to the present invention into a plant cell on the basis of *Agrobacterium* method, particle gun method, electroporation method, or the like and then (ii) as necessary allowing the plant cell to form a callus for production of an individual transgenic plant.

The method for obtaining progeny of a non-human transgenic organism according to the present invention may also be selected depending on the kind of the non-human transgenic organism. An example method for a case of a higher organism is a method for obtaining progeny through mating. A method for a case where the higher organism is a plant may be a method of obtaining progeny with use of an asexual reproduction technique suitable for the kind of the plant.

(Clone of Non-Human Transgenic Organism and Method for Producing Clone)

The present invention covers in its scope producing a clone of a non-human transgenic organism according to the present invention, for example, with use of the non-human transgenic organism. A clone produced, as with the original non-human transgenic organism, contains the full length of a polynucleotide according to the present invention or at least part of the polynucleotide in a genome and allows for expression of any one of the luminescent polypeptides according to the present invention. The term "clone" as used herein is a concept covering an embryonic cell clone and a somatic cell clone.

An example method for producing a clone is a method of nuclear transplantation, that is, a method of transplanting a cell nucleus of a donor into an enucleated unfertilized egg as a recipient. The cell nucleus of a donor may be (1) a somatic cell nucleus of the original non-human transgenic organism or (2) an embryonic cell nucleus derived from the original non-human transgenic organism. The cell nucleus of a donor contains the full length of a polynucleotide according to the present invention or at least part of the polynucleotide in a genome.

The method for nuclear transplantation of a cell nucleus of a donor is not particularly limited. Example methods include (1) a method of cell fusion between an enucleated unfertilized egg and a donor cell and (2) a method of introducing a donor cell into an enucleated unfertilized egg without cell fusion.

[5. Kit]

The present invention also provides a kit including a nucleic acid according to the present invention or a vector according to the present invention.

A kit according to the present invention may include two or more kinds of nucleic acids or vectors, at least one of which is a nucleic acid or vector according to the present invention. The two or more kinds of nucleic acids or vectors preferably include respective base sequences encoding different kinds of luciferase. An embodiment of a kit according to the present invention preferably includes 1) a nucleic acid or vector including a base sequence encoding modified luciferase according to the present invention and 2) a nucleic acid or vector including a base sequence encoding luciferase (e.g., luc2 or mutated luciferase having an improved substrate specificity to luciferin) which specifically recognizes luciferin as a luminescent substrate. Using such a kit enables, for example, observation of the behaviors of a plurality of proteins simultaneously on the basis of a difference in emission wavelength. Accordingly, a kit according to the present invention may be suitably used in a method for detecting light emission which will be described later.

Further, a kit according to the present invention may further include at least one of a luminescent substrate, a pH adjusting agent, a buffer solution, a diluent, a solvent, ATP, $Mg^{2+}$, a disrupted cell suspension, and a cell extract.

Constituent elements of a kit according to the present invention may be contained in a container (e.g., a bottle, a tube, a dish, or the like). The kit preferably includes an instruction manual for using each material. A kit according to the present invention may be a single package containing a plurality of different constituent elements. The constituent elements may each be contained in one of a plurality of different containers in a case where the constituent elements are each in the form of a solution. A kit according to the present invention may include its constituent elements either (i) in a single container as the constituent elements are mixed with each other or (ii) in separate containers. The instruction manual may be printed or written on a medium such as paper or an electronic medium such as a magnetic tape, a computer-readable disc or tape, or a CD-ROM. The instruction manual shows a procedure for achieving the purpose of the kit. In addition, a kit according to the present invention may include an instrument and a reagent that are necessary to carry out the procedure for achieving the purpose of the kit.

[6. Method for Detecting Light Emission]

The present invention also provides a method for detecting light emission, comprising the step of: reacting modified luciferase according to the present invention with at least one other-color luminescent substrate.

In an embodiment, a method according to the present invention for detecting light emission may be used as a method for analyzing an intracellular function. In this case, the method may further comprise a step of introducing modified luciferase according to the present invention into a cell and a step of reacting an other-color luminescent substrate catalyzed by the modified luciferase. For example, a function of an expression regulatory region can be examined by introducing a polynucleotide according to the present invention into a site downstream of a specific expression regulatory region in a DNA, and detecting expression of a modified luciferase on the basis of the presence or absence of light emission caused by a reaction of an other-color luminescent substrate catalyzed by the luciferase.

In another embodiment, a method according to the present invention for detecting light emission may be used as a method for analyzing a protein in a cell. In this case, the method may further comprise a step of introducing, into a cell, a fusion protein consisting of modified luciferase according to the present invention and a protein to be analyzed and a step of reacting an other-color luminescent substrate catalyzed by the modified luciferase. A method according to the present embodiment for detecting light emission may comprise observation of intercellular localization of a protein to be analyzed and (time-lapse) observation of a change in the localization over time.

Further, a method according to the present embodiment for detecting light emission may comprise confirmation not only of localization of a protein but also of simply whether or not the protein has been expressed. Cells to be used are not particularly limited, and may be cells which can be ordinarily used in the field of imaging cells. A protein to be analyzed is not particularly limited either, and may be selected depending on the purpose of the research. The protein may be a protein which originally exists in a cell to be used or may be a heterologous or modified protein which does not originally exist in the cell.

In a case of introducing a fusion protein into a cell, the introduction may be carried out, for example, by a known introduction method. In an example introduction method, a fusion protein, which has been extracellularly purified, is directly introduced into a cell. For example, a microinjection method may be used to inject a fusion protein directly into a cell. Alternatively, a cell may be incubated in a culture solution containing a fusion protein, and the fusion protein may be taken into the cell by endocytosis. In another example introduction method, first, a nucleic acid including a base sequence encoding a fusion protein is introduced into a cell, and then the fusion protein is expressed in the cell. For example, an expression vector including the nucleic acid may be introduced into a cell by a method such as calcium phosphate method, acid lithium method, lipofection method, or electroporation method, and the fusion protein may be expressed from the expression vector. Note that the above-described methods are also applicable to a case in which a protein (e.g., modified luciferase according to the present invention itself, other luciferases, or the like) other than a fusion protein is introduced into a cell.

In an embodiment, a method according to the present invention for detecting light emission may be used as a method for in vivo detection of a cell into which modified luciferase according to the present invention or a fusion protein has been introduced. In an example, the method may comprise a step of producing the cell and then administering the cell into a subject laboratory animal and a step of administering an other-color luminescent substrate catalyzed by the modified luciferase into the laboratory animal so as to cause the other-color luminescent substrate to react in the organism. In this case, the order in which the step of administering the other-color luminescent substrate and the step of administering D-luciferin are carried out is not particularly limited. Further, for example, the method may comprise a step of (i) administering, to the same laboratory animal, a cell into which luciferase that specifically reacts with D-luciferin has been introduced and (ii) then administering D-luciferin into the laboratory animal. In this case, the order in which the step of administering the cell into which the modified luciferase or the fusion protein has been introduced and the step of administering the cell into which the luciferase that specifically reacts with D-luciferin has been introduced are carried out is not particularly limited. Further, the order in which the step of administering the other-color luminescent substrate and the step of administering D-luciferin are carried out is not particularly limited. A method according to the present embodiment for detecting light emission may comprise not only confirmation of localization of administered cells in an organism but also confirmation of the number of cells by quantification of the amount of light emitted.

The step of detecting light emission from an other-color luminescent substrate may be carried out, for example, in accordance with a known detection method. For example, to a cell in which a fusion protein containing modified luciferase is expressed, an other-color luminescent substrate or the like may be provided as appropriate so as to cause the modified luciferase to catalyze a reaction of the other-color luminescent substrate, so that light emitted is detected by an imaging device. The imaging device is, for example, a microscope including a filter for capturing light emission. Using the microscope allows identifying a position where the light emission occurs in the cell and identifying protein localization on the basis of this information. As the imaging device, a microscope having a function of capturing images over time may be used so as to enable time-course observation.

Modified luciferase according to the present invention has an improved substrate specificity to at least one other-color luminescent substrate (e.g., AkaLumine) as compared with to D-luciferin. Accordingly, a method according to the present invention for detecting light emission may be suitably combined with luciferase (e.g., luc2, click beetle green luciferase (CBG) 68, CBG99, Emerald Luc (E-luc), or mutated luciferase having an improved substrate specificity to D-luciferin) which specifically recognizes D-luciferin as a luminescent substrate. Accordingly, in an embodiment, a method according to the present invention for detecting light emission may further comprise a step of reacting D-luciferin with the luciferase which specifically recognizes D-luciferin as a luminescent substrate. Further, the method may comprise a step of introducing the above luciferase into a cell and a step of detecting emission from D-luciferin induced by the above luciferase. Alternatively, the method may further comprise a step of introducing, into a cell, a fusion protein consisting of the above luciferase and a protein to be analyzed and a step of detecting light emission occurring from a reaction of D-luciferin catalyzed by the above luciferase. Note here that the protein fused with the above luciferase may be of the same kind as or a different kind from a protein fused with modified luciferase according to the present invention, depending on the purpose of the detection of light emission.

The detection of light emission may be carried out in vivo or in vitro. In a case of in vivo, the detection of light emission may be carried out with respect to an organism that is not a human (i.e., a non-human organism). The cell may be, for example, an isolated cell, a cell in a tissue, a cell in an organ, or a cell in an individual. The cell may also be a cell in an organ or tissue which has been obtained or artificially cultured from an individual of a multicellular organism. Further, the detection of light emission may be carried out with respect to a progeny (line) of a multicellular organism into which a nucleic acid including a base sequence encoding modified luciferase according to the present invention has been introduced.

Conventional mutated luciferase has a low substrate specificity to at least one other-color luminescent substrate (e.g., AkaLumine) as compared with to D-luciferin, and reacts also with D-luciferin. Accordingly, in light emission detection involving a combination of conventional mutated luciferase and luciferase that specifically recognizes D-luciferin as a luminescent substrate, it is difficult to distinguish between light emission caused by the former and light emission caused by the latter. In contrast, modified luciferase according to the present invention has an improved substrate specificity to at least one other-color luminescent substrate as compared with to D-luciferin (see later described Examples as well). Accordingly, in emission detection involving a combination of modified luciferase according to the present invention and luciferase that specifically recognizes D-luciferin as a luminescent substrate, it is easy to distinguish between light emission caused by the former and light emission caused by the latter.

[7. Method for Designing Modified Luciferase]

The present invention also provides a method for designing modified luciferase whose substrate specificity to at least one other-color luminescent substrate has been improved as compared with to luciferin, the method comprising the step of: causing a mutation at an amino acid in luciferase, the amino acid corresponding to a 347th amino acid in an amino acid sequence represented by SEQ ID NO: 1.

A specific example of a method for causing the mutation is as described above. In the example, a polynucleotide encoding a luminescent polypeptide having a mutation at an amino acid corresponding to the 347th amino acid in the amino acid sequence represented by SEQ ID NO: 1 is produced by a site-directed mutagenesis method and is expressed.

A method according to the present invention for designing modified luciferase may comprise a step of further causing a mutation at an amino acid corresponding to at least one of the amino acid positions described above in addition to the amino acid corresponding to the 347th amino acid in the amino acid sequence represented by SEQ ID NO: 1. A method for causing amino acid mutation may be, for example, the site-directed mutagenesis method described in the section [1. Luminescent Polypeptide].

A method according to the present invention for designing modified luciferase may further comprise, as necessary, a screening step in order to obtain modified luciferase whose substrate specificity to at least one other-color luminescent substrate is particularly excellent as compared with to luciferin. The screening step is achieved, for example, by evaluating obtained modified luciferase with use of the method for evaluating substrate specificity of luciferase described in the section [1. Luminescent Polypeptide].

[8. Summary]

The scope of the present invention encompasses, for example, the following aspects.

1) A polypeptide having a luciferase activity, the polypeptide being defined in any one of (1) to (3) below:
(1) a polypeptide which has (i) a mutation at an amino acid corresponding to a 347th amino acid in an amino acid sequence represented by SEQ ID NO: 1 and (ii) a sequence identity of 85% or more with respect to the amino acid sequence represented by SEQ ID NO: 1; (2) a polypeptide which has (i) a mutation at an amino acid corresponding to the 347th amino acid in the amino acid sequence represented by SEQ ID NO: 1 and (ii) an amino acid sequence which is obtained by substitution, deletion, insertion, and/or addition of 1 to 82 amino acids with respect to the amino acid sequence represented by SEQ ID NO: 1; and (3) a polypeptide which is encoded by a polynucleotide that hybridizes under stringent conditions with a polynucleotide consisting of a sequence complementary to a polynucleotide that encodes a polypeptide having the amino acid sequence represented by SEQ ID NO: 1 and which has a mutation at an amino acid corresponding to the 347th amino acid in the amino acid sequence represented by SEQ ID NO: 1.

2) The polypeptide as set forth in 1), further having a mutation at an amino acid corresponding to a 229th amino acid in the amino acid sequence represented by SEQ ID NO: 1.

3) The polypeptide as set forth in 1) or 2), wherein the mutation at the amino acid corresponding to the 347th amino acid is a substitution to cysteine or asparagine.

4) The polypeptide as set forth in 2) or 3), wherein the mutation at the amino acid corresponding to the 229th amino acid is a substitution to tyrosine or histidine.

5) The polypeptide as set forth in any one of 1) through 4), including an amino acid sequence having a sequence identity of 90% or more with respect to an amino acid sequence represented by any one of SEQ ID NOS: 2 through 7.

6) A nucleic acid including a base sequence encoding a polypeptide as set forth in any one of 1) through 5).

7) A vector including a nucleic acid as set forth in 6).

8) A kit including a nucleic acid as set forth in 6) or a vector as set forth in 7).

9) A method for detecting light emission, comprising the step of: reacting a polypeptide as set forth in any one of 1) through 5) with at least one luminescent substrate other than D-luciferin.

10) A method for designing modified luciferase whose substrate specificity to at least one luminescent substrate other than D-luciferin has been improved as compared with to D-luciferin, the method comprising the step of: causing a mutation at an amino acid in luciferase, the amino acid corresponding to a 347th amino acid in an amino acid sequence represented by SEQ ID NO: 1.

The following will provide Examples to more specifically describe embodiments of the present invention. As a matter of course, the present invention is not limited to Examples provided below, but details of the present invention can be realized in various manners. Further, the present invention is not limited to the embodiments described above, and it may be varied in various ways within the scope of the appended claims. Thus, an embodiment based on a combination of technical means disclosed in different embodiments is encompassed in the technical scope of the present invention. Furthermore, all of the publications and patents cited in the present specification are incorporated herein by reference in their entirety.

EXAMPLES

<1. Modification of luc2 and Evaluation of Substrate Specificity of luc2>

[Materials]

The following were used as luciferases.
(1) luc2 (luciferase derived from *Photinus pyralis*) consisting of an amino acid sequence represented by SEQ ID NO: 1
(2) luc2 variant (S347C)
(3) luc2 variant (S347N)
(4) luc2 variant (N229Y)
(5) luc2 variant (N229H)
(6) luc2 variant (H310Q)
(7) luc2 variant (N229Y+H310Q)
(8) luc2 variant (N229H+H310Q)
(9) luc2 variant (H310Q+S347C)
(10) luc2 variant (H310Q+S347N)
(11) luc2 variant (N229Y+S347C)
(12) luc2 variant (N229H+S347C)
(13) luc2 variant (N229Y+S347N) (SEQ ID NO: 2)
(14) luc2 variant (N229H+S347N) (SEQ ID NO: 3)
(15) luc2 variant (N229Y+H310Q+S347C)
(16) luc2 variant (N229Y+H310Q+S347N) (SEQ ID NO: 4)
(17) luc2 variant (N229H+H310Q+S347C)
(18) luc2 variant (N229H+H310Q+S347N)
(19) luc2 variant a (a in Table 1)
(20) luc2 variant b (b in Table 1) (SEQ ID NO: 5)
(21) luc2 variant c (c in Table 1) (SEQ ID NO: 6)
(22) luc2 variant d (d in Table 1) (SEQ ID NO: 7)

TABLE 1

| a | b | c | d |
|---|---|---|---|
| T39A | T39A | T39A | T39A |
| E48Q | E48Q | E48Q | E48Q |
| I51V | I51V | I51V | I51V |
|  | K68R | K68R | K68R |
|  |  | L86S | L86S |
| Q134R | Q134R | Q134R | Q134R |
| I136V | I136V | I136V | I136V |
|  | N138D |  |  |
| Q147R | Q147R | Q147R | Q147R |
|  | T169A |  |  |
| G175S | G175S | G175S | G175S |
| S185C | S185C |  | S185C |
|  | N229Y | N229Y | N229Y |
| I231N | I231N | I231N | I231N |
|  | L264F |  |  |
|  |  |  | T290A |
|  |  |  | L291P |
| F294C | F294C | F294C | F294C |
| F295L | F295L | F295L | F295L |
| N308S | N308S | N308S | N308S |
| H310R | H310R | H310R | H310R |
| H332R | H332R | H332R | H332R |
| S347N | S347N | S347N | S347N |
| I349V | I349V | I349V | I349V |
|  | L350M | L350M | L350M |
| D357R | D357R | D357R | D357R |
| A361S | A361S | A361S | A361S |
| D377V | D377V | D377V | D377V |
| S456G | S456G | S456G | S456G |
| N463Y | N463Y | N463Y | N463Y |
| K524R | K524R | K524R | K524R |
| L526P | L526P | L526S | L526P |
| I540T | I540T | I540T | I540T |
| G545D | G545D | G545D | G545D |

Mutation(s) was/were introduced by random mutagenesis method and point mutagenesis method into a base sequence of a luc2 gene to produce a luc2 variant into which amino acid mutation(s) has/have been randomly introduced. Specifically, the random mutagenesis method was conducted with use of error-prone PCR. The PCR was conducted with use of: 0.3 µg of a plasmid obtained by integrating a luc2 gene into pRSETb with use of a BamHI restriction enzyme site and an EcoRI restriction enzyme site; 0.1 nmol each of a forward primer and a reverse primer (forward primer: cgggatccgaccATGGAAGATGCCAAAAAC (SEQ ID NO: 9), reverse primer: ggaattcTTACACGGCGATCTTGCC (SEQ ID NO: 10)); 0.5 nmol of $MnCl_2$, and GoTaq Master mix (Promega). Then, the PCR products were cut by BamHI and EcoRI and were inserted into pRSETb so as to be used for transformation of E. coli JM109DE3. The transformed E. coli was plated onto a medium. Then, AkaLumine or D-luciferin was each added to colonies of E. coli, and emission intensities were measured. A colony with a high emission intensity was cultured with use of a LB (ampicillin added) culture solution at 37° C. for 12 hours. Subsequently, DNAs were extracted from E. coli, and the sequence of the luc2 gene, into which mutation(s) had been thus introduced, was read.

The point mutagenesis method was conducted with use of quick change site directed mutagenesis method. 0.6 µg of a plasmid obtained by inserting a luc2 gene into pRSETb with use of a BamHI restriction enzyme site and an EcoRI restriction enzyme site, 0.14 nmol of a phosphorylated primer (GGCCTGACAGAAACAACCnnnGCCATTCT-GATCACCCCC (SEQ ID NO: 11): either A, T, G, or C is at n), Taq DNA ligase (new England biolab) and a buffer thereof, Pfu DNA polymerase (agilent) and a buffer thereof, and dNTPs were added to conduct PCR. Then, 0.5 µl of DpnI (New England Biolab) was added and treatment was conducted at 37° C. for 40 minutes. Subsequently, the resultant product was used for transformation of E. coli JM109DE3. The transformed E. coli was plated onto a medium. Then, AkaLumine or D-luciferin was each added to colonies of E. coli, and emission intensities were measured. A colony with a high emission intensity was cultured with use of a LB (ampicillin added) culture solution at 37° C. for 12 hours. Subsequently, DNAs were extracted from E. coli, and the sequence of the luc2 gene, into which mutation(s) had been thus introduced, was read.

[Procedure]

A plasmid pcDNA3 was treated with use of BamHI and EcoRI, and genes encoding the respective luciferases above were each inserted into the plasmid pcDNA3 to produce plasmids for transfection.

HeLa S3 cells were used as mammalian cells to be transfected. For each of the luciferases above, HeLa S3 cells which had been cultured in D-MEM (low glucose, containing 10% FBS and 1% penicillin streptomycin, Wako Pure Chemical Industries, Ltd.) and were in an 80% confluent state were mixed with a transfection reagent (Polyethylenimine, Linear (MW 25,000, Polysciences, Inc)) and the plasmid for transfection (0.3 µg) to conduct transfection.

24 hours after the transfection, the cells were dissociated through trypsinization, and were suspended in DMEM/F12 (10% FBS, gibco). Subsequently, centrifugation was conducted to remove the supernatant, and then the cells were resuspended in 1 mL DMEM/F12 so as to be used as luciferase-expressing cells.

In 1.5 mL Eppendorf tube, 20 µL of the produced luciferase-expressing cells and 80 µL of a substrate solution (prepared with pH 7.4 PBS) were mixed, and light emission from the obtained mixture was measured for one minute (with use of a luminometer AB-2280 manufactured by ATTO Corporation). An integrated value of the values thus measured within one minute was defined as the emission intensity.

As the substrate solution, AkaLumine or D-luciferin (80 µM each) was added. Results of the measurement of emission intensity are shown below in Table 2 as relative values with respect to 1.0 which is an emission intensity obtained in a case where AkaLumine was added to a sample of luc2.

TABLE 2

|  | AkaLumine | D-luciferin | AkaLumine/ D-luciferin |
|---|---|---|---|
| Luc2 | 1.0 | $5.5 \times 10^{-1}$ | 1.8 |
| Variant a | 2.2 | $6.1 \times 10^{-1}$ | $3.6 \times 10^{-2}$ |
| Variant b | 2.4 | not detected | — |
| Variant c | 6.8 | not detected | — |
| Variant d | 6.1 | $1.8 \times 10^{-3}$ | $3.4 \times 10^{3}$ |

Subsequently, with use of D-luciferin, AkaLumine, AkaLumine-OH, 6-AkaLumine, 0-AkaLumine, monoene NMe2, monoene NH2, monoene OH, and biphenyl as substrates, specificity to each of these substrates was evaluated. The substrates are respectively represented by the following chemical formulae. Each substrate solution contains a single kind of substrate.

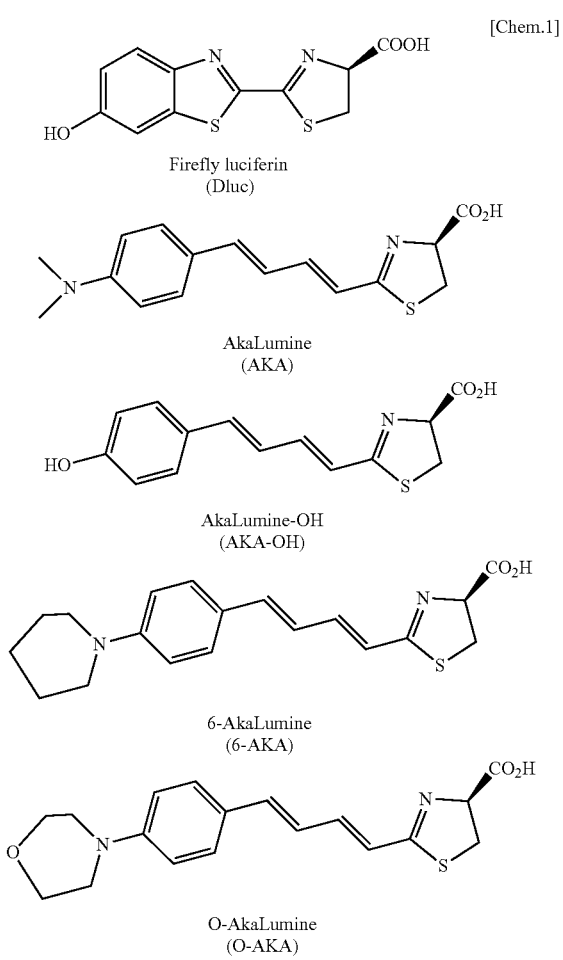

[Chem.1]

Firefly luciferin
(Dluc)

AkaLumine
(AKA)

AkaLumine-OH
(AKA-OH)

6-AkaLumine
(6-AKA)

O-AkaLumine
(O-AKA)

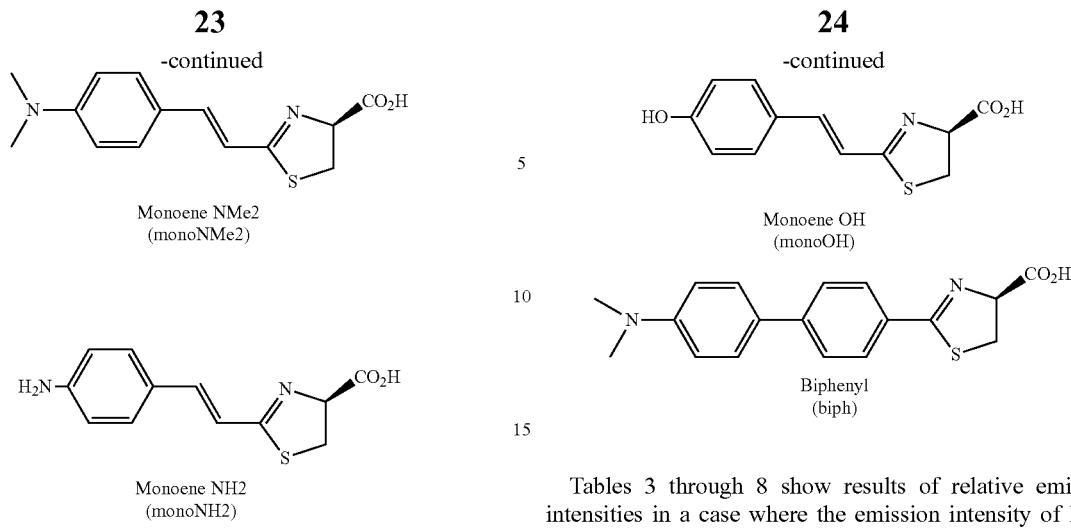

Monoene NMe2 (monoNMe2)

Monoene OH (monoOH)

Monoene NH2 (monoNH2)

Biphenyl (biph)

Tables 3 through 8 show results of relative emission intensities in a case where the emission intensity of D-luciferin is defined as 1.

TABLE 3

<Difference in substrate specificity depending on introduction of mutation to S347>

| | luc2 | | S347C | | S347N |
|---|---|---|---|---|---|
| Dluc | 1.0 | Dluc | 1.0 | Dluc | 1.0 |
| AKA | $2.6 \times 10^{-1}$ | AKA | $2.8 \times 10$ | AKA | $2.9 \times 10$ |
| AKA-OH | not detected | AKA-OH | $3.0 \times 10^{-2}$ | AKA-OH | $2.0 \times 10^{-1}$ |
| 6-AKA | $1.6 \times 10^{-1}$ | 6-AKA | $1.5 \times 10$ | 6-AKA | $2.9 \times 10$ |
| O-AKA | $8.4 \times 10^{-3}$ | O-AKA | $1.3 \times 10^{-1}$ | O-AKA | 2.1 |
| monoNMe2 | $1.1 \times 10^{-1}$ | monoNMe2 | 5.1 | monoNMe2 | $1.5 \times 10$ |
| monoNH2 | $3.0 \times 10^{-3}$ | monoNH2 | $5.9 \times 10^{-2}$ | monoNH2 | $1.0 \times 10^{-1}$ |
| monoOH | $1.8 \times 10^{-3}$ | monoOH | $2.2 \times 10^{-2}$ | monoOH | $7.4 \times 10^{-2}$ |
| biph | $1.4 \times 10^{-2}$ | biph | $5.7 \times 10^{-1}$ | biph | $2.7 \times 10^{-1}$ |

TABLE 4

<Difference in substrate specificity depending on introduction of N229 mutation and H310 mutation>

| | N229Y | | N229H | | H310Q |
|---|---|---|---|---|---|
| Dluc | 1.0 | Dluc | 1.0 | Dluc | 1.0 |
| AKA | $1.1 \times 10$ | AKA | 3.8 | AKA | 1.2 |
| AKA-OH | $3.4 \times 10^{-3}$ | AKA-OH | $1.8 \times 10^{-3}$ | AKA-OH | $4.9 \times 10^{-4}$ |
| 6-AKA | 1.6 | 6-AKA | 1.9 | 6-AKA | $4.9 \times 10^{-1}$ |
| O-AKA | $2.3 \times 10^{-1}$ | O-AKA | $3.1 \times 10^{-2}$ | O-AKA | $1.1 \times 10^{-2}$ |
| monoNMe2 | 1.6 | monoNMe2 | $2.7 \times 10^{-1}$ | monoNMe2 | $1.3 \times 10^{-1}$ |
| monoNH2 | $7.6 \times 10^{-3}$ | monoNH2 | $4.8 \times 10^{-3}$ | monoNH2 | $1.4 \times 10^{-3}$ |
| monoOH | $7.5 \times 10^{-4}$ | monoOH | not detected | monoOH | $4.7 \times 10^{-4}$ |
| biph | $1.3 \times 10^{-1}$ | biph | $7.7 \times 10^{-2}$ | biph | $1.9 \times 10^{-2}$ |

TABLE 5

<Difference in substrate specificity depending on introduction of S347 mutation to N229 mutation>

| | N229Y_S347N | | N229H_S347N | | N229Y_S347C | | N229H_S347C |
|---|---|---|---|---|---|---|---|
| Dluc | 1.0 | Dluc | 1.0 | Dluc | 1.0 | Dluc | 1.0 |
| AKA | $6.4 \times 10^{3}$ | AKA | $1.7 \times 10^{3}$ | AKA | $2.9 \times 10^{2}$ | AKA | $1.5 \times 10^{2}$ |
| AKA-OH | 2.1 | AKA-OH | 0.9 | AKA-OH | $7.2 \times 10^{-2}$ | AKA-OH | $4.4 \times 10^{-2}$ |
| 6-AKA | $9.6 \times 10^{2}$ | 6-AKA | $8.5 \times 10^{2}$ | 6-AKA | $1.6 \times 10$ | 6-AKA | $1.1 \times 10^{2}$ |
| O-AKA | $2.9 \times 10^{2}$ | O-AKA | 6.3 | O-AKA | $1.9 \times 10^{-1}$ | O-AKA | $3.1 \times 10^{-1}$ |
| monoNMe2 | $2.4 \times 10^{2}$ | monoNMe2 | $4.3 \times 10$ | monoNMe2 | $1.7 \times 10$ | monoNMe2 | $1.2 \times 10$ |
| monoNH2 | 1.7 | monoNH2 | $4.3 \times 10^{-1}$ | monoNH2 | $9.1 \times 10^{-2}$ | monoNH2 | $5.2 \times 10^{-2}$ |
| monoOH | $1.4 \times 10^{-2}$ | monoOH | not detected | monoOH | $2.6 \times 10^{-3}$ | monoOH | $6.8 \times 10^{-4}$ |
| biph | 6.9 | biph | 4.9 | biph | 3.1 | biph | 5.6 |

TABLE 6

<Difference in substrate specificity depending on introduction of S347 mutation or N229 mutation to H310 mutation>

| | H310Q_S347N | | H310Q_S347C | | N229Y_H310Q | | N229H_H310Q |
|---|---|---|---|---|---|---|---|
| Dluc | 1.0 | Dluc | 1.0 | Dluc | 1.0 | Dluc | 1.0 |
| AKA | $9.4 \times 10$ | AKA | $1.4 \times 10$ | AKA | $1.2 \times 10$ | AKA | 4.3 |
| AKA-OH | $8.1 \times 10^{-2}$ | AKA-OH | $2.7 \times 10^{-3}$ | AKA-OH | $6.6 \times 10^{-3}$ | AKA-OH | $2.7 \times 10^{-3}$ |
| 6-AKA | $8.6 \times 10$ | 6-AKA | 5.4 | 6-AKA | 2.2 | 6-AKA | 2.9 |
| O-AKA | 1.1 | O-AKA | $1.2 \times 10^{-1}$ | O-AKA | $3.9 \times 10^{-1}$ | O-AKA | $5.9 \times 10^{-2}$ |
| monoNMe2 | $2.6 \times 10$ | monoNMe2 | 3.0 | monoNMe2 | 1.2 | monoNMe2 | $6.0 \times 10^{-1}$ |
| monoNH2 | $6.0 \times 10^{-2}$ | monoNH2 | $7.3 \times 10^{-3}$ | monoNH2 | $1.1 \times 10^{-2}$ | monoNH2 | $3.9 \times 10^{-3}$ |
| monoOH | $2.0 \times 10^{-1}$ | monoOH | $2.7 \times 10^{-3}$ | monoOH | $6.0 \times 10^{-4}$ | monoOH | not detected |
| biph | $8.8 \times 10^{-1}$ | biph | $4.4 \times 10^{-1}$ | biph | $2.2 \times 10^{-1}$ | biph | $9.3 \times 10^{-2}$ |

TABLE 7

<Difference in substrate specificity depending on combination of N229 mutation, H310 mutation, and S347 mutation>

| | N229H_H310Q_S347N | | N229Y_H310Q_S347C | | N229Y_H310Q_S347N | | N229H_H310Q_S347C |
|---|---|---|---|---|---|---|---|
| Dluc | 1.0 | Dluc | 1.0 | Dluc | 1.0 | Dluc | 1.0 |
| AKA | $2.5 \times 10^2$ | AKA | $3.3 \times 10^2$ | AKA | $4.1 \times 10^3$ | AKA | $7.4 \times 10$ |
| AKA-OH | $2.1 \times 10^{-1}$ | AKA-OH | $8.4 \times 10^{-2}$ | AKA-OH | 1.4 | AKA-OH | $2.5 \times 10^{-2}$ |
| 6-AKA | $1.9 \times 10^2$ | 6-AKA | $5.2 \times 10$ | 6-AKA | $1.1 \times 10^3$ | 6-AKA | $3.6 \times 10$ |
| O-AKA | 2.2 | O-AKA | $4.4 \times 10^{-1}$ | O-AKA | $2.1 \times 10^{-3}$ | O-AKA | $1.5 \times 10^{-2}$ |
| monoNMe2 | $1.3 \times 10$ | monoNMe2 | 7.3 | monoNMe2 | $6.4 \times 10$ | monoNMe2 | 8.9 |
| monoNH2 | $1.2 \times 10^{-1}$ | monoNH2 | $7.4 \times 10^{-2}$ | monoNH2 | $7.3 \times 10^{-1}$ | monoNH2 | $3.7 \times 10^{-2}$ |
| monoOH | $7.8 \times 10^{-3}$ | monoOH | $2.0 \times 10^{-3}$ | monoOH | $1.3 \times 10^{-1}$ | monoOH | not detected |
| biph | 2.0 | biph | 3.4 | biph | $1.3 \times 10$ | biph | 1.7 |

TABLE 8

<Difference in substrate specificity among variants a, b, c, and d>

| | Variant a | | Variant b | | Variant c | | Variant d |
|---|---|---|---|---|---|---|---|
| Dluc | 1.0 | Dluc | 1.0 | Dluc | 1.0 | Dluc | 1.0 |
| AKA | $1.8 \times 10^2$ | AKA | $2.4 \times 10^3$ | AKA | $9.0 \times 10^3$ | AKA | $3.4 \times 10^3$ |
| AKA-OH | $2.8 \times 10^{-1}$ | AKA-OH | 0.9 | AKA-OH | 1.8 | AKA-OH | $9.8 \times 10^{-1}$ |
| 6-AKA | $1.4 \times 10^2$ | 6-AKA | $8.1 \times 10^2$ | 6-AKA | $1.8 \times 10^3$ | 6-AKA | $1.5 \times 10^3$ |
| O-AKA | 3.0 | O-AKA | $3.2 \times 10$ | O-AKA | $2.6 \times 10$ | O-AKA | $2.2 \times 10$ |
| monoNMe2 | 5.4 | monoNMe2 | $1.3 \times 10$ | monoNMe2 | $1.7 \times 10$ | monoNMe2 | 6.6 |
| monoNH2 | $4.5 \times 10^{-2}$ | monoNH2 | $1.2 \times 10^{-1}$ | monoNH2 | $1.8 \times 10^{-1}$ | monoNH2 | $1.3 \times 10^{-1}$ |
| monoOH | not detected | monoOH | $1.5 \times 10^{-2}$ | monoOH | $1.1 \times 10^{-1}$ | monoOH | $7.1 \times 10^{-2}$ |
| biph | 1.1 | biph | 3.1 | biph | 4.1 | biph | 7.5 |

<2. Comparison of Emission Intensities of Luciferases>

80 μM of AkaLumine was added to HeLa S3 cells (inoculated onto a 35 mm glass bottomed dish), in which the variant c luciferase or the variant d luciferase each fused with a fluorescent protein Venus had been transiently expressed. With use of a luminescence microscope LV200 (Olympus), an emission intensity and a fluorescence intensity of Venus were measured on a cell-by-cell basis. Subsequently, the emission intensity was normalized with use of the fluorescence intensity to quantify the amount of the protein, and the emission intensity of each luciferase was measured.

HeLa S3 cells which had been cultured in D-MEM (low glucose, containing 10% FBS and 1% penicillin streptomycin, Wako Pure Chemical Industries, Ltd.) and in an 80% confluent state were mixed with a transfection reagent (Polyethylenimine, Linear (MW 25,000, Polysciences, Inc)) and DNA (0.3 μg) in which each luciferase had been inserted, and transfection was conducted. A plasmid DNA obtained by inserting "KpnI restriction enzyme site—Venus—BamHI restriction enzyme site—luciferase—EcoRI restriction enzyme site" into pcDNA3 was used. 24 hours after the transfection, obtained cells were subjected, as cells expressing a fusion protein of "Venus—each luciferase", to observation of fluorescence of Venus with use of LV200 (×40 objective lens). Then, AkaLumine (final concentration: 80 μL) was immediately added, and light emission from the cells were observed for 20 minutes.

From a microscopic image obtained, a fluorescence intensity and an emission intensity were calculated for each of 10 or more cells with use of image analysis software imageJ, and a ratio of an emission intensity to a fluorescence intensity of each luciferase was used as data of an emission intensity per unit protein. It was thus confirmed that the relationship between fluorescence intensity and emission intensity is linear.

Further, HeLa S3 cells, which had been produced in a similar manner to the above and in which luc2 luciferase, the variant c luciferase, or the variant d luciferase each fused with a fluorescent protein Venus had been transiently expressed (the HeLa S3 cells were inoculated onto a 35 mm glass bottomed dish), were subjected to fluorescence observation with use of LV200. Results of the observation are shown in FIG. 1. Since it has been confirmed above that the relationship between fluorescence intensity and emission intensity is linear, it is assumed that a fluorescence intensity and an expression level of "Venus—each luciferase" are correlated with each other. It was thus revealed from the fluorescence observation that "Venus—luc2 variant" has a higher expression efficiency (there are clearly a greater number of cells with a high fluorescence intensity) as compared with "Venus—luc2".

INDUSTRIAL APPLICABILITY

The present invention is applicable to various fields such as bio-life science, medical science, and pharmaceutical science.

The invention claimed is:

1. A polypeptide having a luciferase activity, the polypeptide being defined in any one of (1) through (3) below:
   (1) a polypeptide which has (i) a mutation at an amino acid corresponding to a 347th amino acid in an amino acid sequence as set forth in SEQ ID NO: 1 and (ii) a sequence identity of 85% or more with respect to the amino acid sequence as set forth in SEQ ID NO: 1;
   (2) a polypeptide which has (i) a mutation at an amino acid corresponding to the 347th amino acid in the amino acid sequence as set forth in SEQ ID NO: 1 and (ii) an amino acid sequence which is obtained by substitution, deletion, insertion, and/or addition of 1 to 82 amino acids with respect to the amino acid sequence as set forth in SEQ ID NO: 1; and
   (3) a polypeptide which is encoded by a polynucleotide that hybridizes under a stringent condition with a polynucleotide having a sequence complementary to a polynucleotide that encodes a polypeptide having the amino acid sequence as set forth in SEQ ID NO: 1 and which has a mutation at an amino acid corresponding to the 347th amino acid in the amino acid sequence as set forth in SEQ ID NO: 1, wherein the stringent conditions are conducted by incubating at 65° C. for 8 to 16 hours together with a probe, in a solution that contains 6×SSC (composition of 1×SSC: 0.15 M of sodium chloride, 0.015 M of sodium citrate, pH 7.0), 0.5% of SDS, 5×Denhardt's solution, and 100 mg/mL of herring sperm DNA;

wherein the mutation at the amino acid corresponding to the 347th amino acid is a substitution to cysteine or asparagine;

wherein when the mutation at the amino acid corresponding to the 347th amino acid is a substitution to cysteine, the polypeptide further comprises a mutation at an amino acid corresponding to a 229th amino acid which is substitution to tyrosine or histidine; and wherein the polypeptide has improved substrate specificity to AkaLumine as compared to D-luciferin.

2. The polypeptide as set forth in claim 1, wherein when the mutation at the amino acid corresponding to the 347th amino acid is a substitution to asparagine, the polypeptide further comprises a mutation at an amino acid corresponding to a 229th amino acid in the amino acid sequence as set forth in SEQ ID NO: 1 which is substitution to tyrosine or histidine.

3. The polypeptide as set forth in claim 1, comprising an amino acid sequence having a sequence identity of 90% or more with respect to the amino acid sequence as set forth in any one of SEQ ID NOS: 2 through 7.

4. The polypeptide as set forth in claim 1, wherein the polypeptide has improved substrate specificity to AkaLumine, 6-AkaLumine, and monoene NMe2 as compared to D-luciferin.

5. A method for detecting light emission, comprising the step of:
  reacting the polypeptide as set forth in claim 1 with at least one luminescent substrate other than D-luciferin.

* * * * *

SEQUENCE LISTING

```
<160> NUMBER OF SEQ ID NOS: 11

<210> SEQ ID NO 1
<211> LENGTH: 550
<212> TYPE: PRT
<213> ORGANISM: Photinus pyralis

<400> SEQUENCE: 1

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300
```

```
Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
            325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
        370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
        530                 535                 540

Gly Gly Lys Ile Ala Val
545                 550

<210> SEQ ID NO 2
<211> LENGTH: 550
<212> TYPE: PRT
<213> ORGANISM: Artificial Sequence
<220> FEATURE:
<223> OTHER INFORMATION: Modified Luciferase

<400> SEQUENCE: 2

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65              70                  75                  80

Cys Ser Glu Asn Ser Leu Gln Phe Phe Met Pro Val Leu Gly Ala Leu
            85                  90                  95

Phe Ile Gly Val Ala Val Ala Pro Ala Asn Asp Ile Tyr Asn Glu Arg
        100                 105                 110
```

-continued

```
Glu Leu Leu Asn Ser Met Gly Ile Ser Gln Pro Thr Val Phe Val
            115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
210                 215                 220

Pro Ile Phe Gly Tyr Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Asn Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
```

Gly Gly Lys Ile Ala Val
545             550

<210> SEQ ID NO 3
<211> LENGTH: 550
<212> TYPE: PRT
<213> ORGANISM: Artificial Sequence
<220> FEATURE:
<223> OTHER INFORMATION: Modified Luciferase

<400> SEQUENCE: 3

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
210                 215                 220

Pro Ile Phe Gly His Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Asn Ala Ile Leu Ile Thr

```
            340              345              350
Pro Glu Gly Asp Asp Lys Pro Gly Ala Val Gly Lys Val Val Pro Phe
        355                  360                  365

Phe Glu Ala Lys Val Val Asp Leu Asp Thr Gly Lys Thr Leu Gly Val
        370                  375                  380

Asn Gln Arg Gly Glu Leu Cys Val Arg Gly Pro Met Ile Met Ser Gly
385                 390                  395                  400

Tyr Val Asn Asn Pro Glu Ala Thr Asn Ala Leu Ile Asp Lys Asp Gly
                405                  410                  415

Trp Leu His Ser Gly Asp Ile Ala Tyr Trp Asp Glu Asp Glu His Phe
                420                  425                  430

Phe Ile Val Asp Arg Leu Lys Ser Leu Ile Lys Tyr Lys Gly Tyr Gln
            435                  440                  445

Val Ala Pro Ala Glu Leu Glu Ser Ile Leu Leu Gln His Pro Asn Ile
        450                  455                  460

Phe Asp Ala Gly Val Ala Gly Leu Pro Asp Asp Asp Ala Gly Glu Leu
465                 470                  475                  480

Pro Ala Ala Val Val Val Leu Glu His Gly Lys Thr Met Thr Glu Lys
                485                  490                  495

Glu Ile Val Asp Tyr Val Ala Ser Gln Val Thr Thr Ala Lys Lys Leu
                500                  505                  510

Arg Gly Gly Val Val Phe Val Asp Glu Val Pro Lys Gly Leu Thr Gly
            515                  520                  525

Lys Leu Asp Ala Arg Lys Ile Arg Glu Ile Leu Ile Lys Ala Lys Lys
        530                  535                  540

Gly Gly Lys Ile Ala Val
545                 550

<210> SEQ ID NO 4
<211> LENGTH: 550
<212> TYPE: PRT
<213> ORGANISM: Artificial Sequence
<220> FEATURE:
<223> OTHER INFORMATION: Modified Luciferase

<400> SEQUENCE: 4

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
```

```
                145                 150                 155                 160
        Phe Gln Ser Met Tyr Thr Phe Val Thr Ser His Leu Pro Pro Gly Phe
                        165                 170                 175
        Asn Glu Tyr Asp Phe Val Pro Glu Ser Phe Asp Arg Asp Lys Thr Ile
                        180                 185                 190
        Ala Leu Ile Met Asn Ser Ser Gly Ser Thr Gly Leu Pro Lys Gly Val
                        195                 200                 205
        Ala Leu Pro His Arg Thr Ala Cys Val Arg Phe Ser His Ala Arg Asp
        210                 215                 220
        Pro Ile Phe Gly Tyr Gln Ile Ile Pro Asp Thr Ala Ile Leu Ser Val
        225                 230                 235                 240
        Val Pro Phe His His Gly Phe Gly Met Phe Thr Thr Leu Gly Tyr Leu
                        245                 250                 255
        Ile Cys Gly Phe Arg Val Val Leu Met Tyr Arg Phe Glu Glu Glu Leu
                        260                 265                 270
        Phe Leu Arg Ser Leu Gln Asp Tyr Lys Ile Gln Ser Ala Leu Leu Val
                        275                 280                 285
        Pro Thr Leu Phe Ser Phe Phe Ala Lys Ser Thr Leu Ile Asp Lys Tyr
                        290                 295                 300
        Asp Leu Ser Asn Leu Gln Glu Ile Ala Ser Gly Gly Ala Pro Leu Ser
        305                 310                 315                 320
        Lys Glu Val Gly Glu Ala Val Ala Lys Arg Phe His Leu Pro Gly Ile
                        325                 330                 335
        Arg Gln Gly Tyr Gly Leu Thr Glu Thr Thr Asn Ala Ile Leu Ile Thr
                        340                 345                 350
        Pro Glu Gly Asp Asp Lys Pro Gly Ala Val Gly Lys Val Val Pro Phe
                        355                 360                 365
        Phe Glu Ala Lys Val Val Asp Leu Asp Thr Gly Lys Thr Leu Gly Val
                        370                 375                 380
        Asn Gln Arg Gly Glu Leu Cys Val Arg Gly Pro Met Ile Met Ser Gly
        385                 390                 395                 400
        Tyr Val Asn Asn Pro Glu Ala Thr Asn Ala Leu Ile Asp Lys Asp Gly
                        405                 410                 415
        Trp Leu His Ser Gly Asp Ile Ala Tyr Trp Asp Glu Asp Glu His Phe
                        420                 425                 430
        Phe Ile Val Asp Arg Leu Lys Ser Leu Ile Lys Tyr Lys Gly Tyr Gln
                        435                 440                 445
        Val Ala Pro Ala Glu Leu Glu Ser Ile Leu Leu Gln His Pro Asn Ile
        450                 455                 460
        Phe Asp Ala Gly Val Ala Gly Leu Pro Asp Asp Asp Ala Gly Glu Leu
        465                 470                 475                 480
        Pro Ala Ala Val Val Val Leu Glu His Gly Lys Thr Met Thr Glu Lys
                        485                 490                 495
        Glu Ile Val Asp Tyr Val Ala Ser Gln Val Thr Thr Ala Lys Lys Leu
                        500                 505                 510
        Arg Gly Gly Val Val Phe Val Asp Glu Val Pro Lys Gly Leu Thr Gly
                        515                 520                 525
        Lys Leu Asp Ala Arg Lys Ile Arg Glu Ile Leu Ile Lys Ala Lys Lys
        530                 535                 540
        Gly Gly Lys Ile Ala Val
        545                 550

<210> SEQ ID NO 5
```

<211> LENGTH: 550
<212> TYPE: PRT
<213> ORGANISM: Artificial Sequence
<220> FEATURE:
<223> OTHER INFORMATION: Modified Luciferase

<400> SEQUENCE: 5

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Ala Ile Ala Phe Thr Asp Ala His Ile Gln
        35                  40                  45

Val Asp Val Thr Tyr Ala Glu Tyr Phe Glu Met Ser Val Arg Leu Ala
 50                  55                  60

Glu Ala Met Arg Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Arg Lys Val Leu Asp Val Gln Lys Lys Leu Pro
130                 135                 140

Ile Ile Arg Lys Ile Ile Ile Met Asp Ser Lys Thr Asp Tyr Gln Gly
145                 150                 155                 160

Phe Gln Ser Met Tyr Thr Phe Val Ala Ser His Leu Pro Pro Ser Phe
                165                 170                 175

Asn Glu Tyr Asp Phe Val Pro Glu Cys Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Tyr Gln Asn Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Phe Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Cys Leu Ala Lys Ser Thr Leu Ile Asp Lys Tyr
    290                 295                 300

Asp Leu Ser Ser Leu Arg Glu Ile Ala Ser Gly Gly Ala Pro Leu Ser
305                 310                 315                 320

Lys Glu Val Gly Glu Ala Val Ala Lys Arg Phe Arg Leu Pro Gly Ile
                325                 330                 335

Arg Gln Gly Tyr Gly Leu Thr Glu Thr Thr Asn Ala Val Met Ile Thr
            340                 345                 350

Pro Glu Gly Asp Arg Lys Pro Gly Ser Val Gly Lys Val Val Pro Phe
        355                 360                 365

Phe Glu Ala Lys Val Val Asp Leu Val Thr Gly Lys Thr Leu Gly Val
    370                 375                 380
```

```
Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Gly Ile Leu Leu Gln His Pro Tyr Ile
    450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Arg Gly Pro Thr Gly
            515                 520                 525

Lys Leu Asp Ala Arg Lys Ile Arg Glu Ile Leu Thr Lys Ala Lys Lys
    530                 535                 540

Asp Gly Lys Ile Ala Val
545                 550

<210> SEQ ID NO 6
<211> LENGTH: 550
<212> TYPE: PRT
<213> ORGANISM: Artificial Sequence
<220> FEATURE:
<223> OTHER INFORMATION: Modified Luciferase

<400> SEQUENCE: 6

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Ala Ile Ala Phe Thr Asp Ala His Ile Gln
        35                  40                  45

Val Asp Val Thr Tyr Ala Glu Tyr Phe Glu Met Ser Val Arg Leu Ala
    50                  55                  60

Glu Ala Met Arg Arg Tyr Gly Leu Asn Thr His Arg Ile Val Val
65                  70                  75                  80

Cys Ser Glu Asn Ser Ser Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Arg Lys Val Leu Asn Val Gln Lys Lys Leu Pro
    130                 135                 140

Ile Ile Arg Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Ser Phe
                165                 170                 175

Asn Glu Tyr Asp Phe Val Pro Glu Ser Phe Asp Arg Asp Lys Thr Ile
            180                 185                 190
```

```
Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
        210                 215                 220

Pro Ile Phe Gly Tyr Gln Asn Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Cys Leu Ala Lys Ser Thr Leu Ile Asp Lys Tyr
    290                 295                 300

Asp Leu Ser Ser Leu Arg Glu Ile Ala Ser Gly Gly Ala Pro Leu Ser
305                 310                 315                 320

Lys Glu Val Gly Glu Ala Val Ala Lys Arg Phe Arg Leu Pro Gly Ile
                325                 330                 335

Arg Gln Gly Tyr Gly Leu Thr Glu Thr Thr Asn Ala Val Met Ile Thr
            340                 345                 350

Pro Glu Gly Asp Arg Lys Pro Gly Ser Val Gly Lys Val Val Pro Phe
        355                 360                 365

Phe Glu Ala Lys Val Val Asp Leu Val Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Gly Ile Leu Leu Gln His Pro Tyr Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Arg Gly Ser Thr Gly
        515                 520                 525

Lys Leu Asp Ala Arg Lys Ile Arg Glu Ile Leu Thr Lys Ala Lys Lys
    530                 535                 540

Asp Gly Lys Ile Ala Val
545                 550
```

<210> SEQ ID NO 7
<211> LENGTH: 550
<212> TYPE: PRT
<213> ORGANISM: Artificial Sequence
<220> FEATURE:
<223> OTHER INFORMATION: Modified Luciferase

<400> SEQUENCE: 7

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Ala Ile Ala Phe Thr Asp Ala His Ile Gln
            35                  40                  45

Val Asp Val Thr Tyr Ala Glu Tyr Phe Glu Met Ser Val Arg Leu Ala
    50                  55                  60

Glu Ala Met Arg Arg Tyr Gly Leu Asn Thr Asn His Arg Ile Val Val
65                  70                  75                  80

Cys Ser Glu Asn Ser Ser Gln Phe Phe Met Pro Val Leu Gly Ala Leu
                    85                  90                  95

Phe Ile Gly Val Ala Val Ala Pro Ala Asn Asp Ile Tyr Asn Glu Arg
                100                 105                 110

Glu Leu Leu Asn Ser Met Gly Ile Ser Gln Pro Thr Val Val Phe Val
            115                 120                 125

Ser Lys Lys Gly Leu Arg Lys Val Leu Asn Val Gln Lys Lys Leu Pro
    130                 135                 140

Ile Ile Arg Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Ser Phe
                165                 170                 175

Asn Glu Tyr Asp Phe Val Pro Glu Cys Phe Asp Arg Asp Lys Thr Ile
                180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
    210                 215                 220

Pro Ile Phe Gly Tyr Gln Asn Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
            275                 280                 285

Pro Ala Pro Phe Ser Cys Leu Ala Lys Ser Thr Leu Ile Asp Lys Tyr
    290                 295                 300

Asp Leu Ser Ser Leu Arg Glu Ile Ala Ser Gly Gly Ala Pro Leu Ser
305                 310                 315                 320

Lys Glu Val Gly Glu Ala Val Ala Lys Arg Phe Arg Leu Pro Gly Ile
                325                 330                 335

Arg Gln Gly Tyr Gly Leu Thr Glu Thr Thr Asn Ala Val Met Ile Thr
            340                 345                 350

Pro Glu Gly Asp Arg Lys Pro Gly Ser Val Gly Lys Val Val Pro Phe
    355                 360                 365

Phe Glu Ala Lys Val Val Asp Leu Val Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415
```

```
Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Gly Ile Leu Leu Gln His Pro Tyr Ile
    450                 455                 460

Phe Asp Ala Gly Val Ala Gly Leu Pro Asp Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Arg Gly Pro Thr Gly
        515                 520                 525

Lys Leu Asp Ala Arg Lys Ile Arg Glu Ile Leu Thr Lys Ala Lys Lys
    530                 535                 540

Asp Gly Lys Ile Ala Val
545                 550

<210> SEQ ID NO 8
<211> LENGTH: 1653
<212> TYPE: DNA
<213> ORGANISM: Artificial Sequence
<220> FEATURE:
<223> OTHER INFORMATION: Modified Luciferase

<400> SEQUENCE: 8
atggaagatg ccaaaaacat taagaagggc ccagcgccat tctacccact cgaagacggg      60
accgccggcg agcagctgca caaagccatg aagcgctacg ccctggtgcc cggcaccatc     120
gcctttaccg acgcacatat cgaggtggac attacctacg ccgagtactt cgagatgagc     180
gttcggctgg cagaagctat gaagcgctat gggctaaata aaaccatcg atcgtggtg      240 tgcagcgaga atagcttgca gttcttcatg cccgtgttgg gtgccctgtt catcggtgtg     300
gctgtggccc cagctaacga catctacaac gagcgcgagc tgctgaacag catgggcatc     360
agccagccca ccgtcgtatt cgtgagcaag aaagggctgc aaaagatcct caacgtgcaa     420
aagaagctac cgatcataca aaagatcatc atcatggata gcaagaccga ctaccagggc     480
ttccaaagca tgtacacctt cgtgacttcc catttgccac ccggcttcaa cgagtacgac     540
ttcgtgcccg agagcttcga ccgggacaaa accatcgccc tgatcatgaa cagtagtggc     600
agtaccggat tgcccaaggg cgtagcccta ccgcaccgca ccgcttgtgt ccgattcagt     660
catgcccgcg accccatctt cggcaaccag atcatccccg acaccgctat cctcagcgtg     720
gtgccatttc accacggctt cggcatgttc accacgctgg gctacttgat ctgcggcttt     780
cgggtcgtgc tcatgtaccg cttcgaggag gagctattct tgcgcagctt gcaagactat     840
aagattcaat ctgccctgct ggtgcccaca ctatttagct tcttcgctaa gagcactctc     900
atcgacaagt acgacctaag caacttgcac gagatcgcca gcggcgggc gccgctcagc     960 aaggaggtag gtgaggccgt ggccaaacgc ttccacctac caggcatccg ccagggctac    1020
ggcctgacag aaacaaccag cgccattctg atcacccccg aagggacga caagcctggc    1080 gcagtaggca aggtggtgcc cttcttcgag gctaaggtgg tggacttgga caccggtaag    1140
acactgggtg tgaaccagcg cggcgagctg tgcgtccgtg gccccatgat catgagcggc    1200
tacgttaaca cccccgaggc tacaaacgct ctcatcgaca aggacggctg gctgcacagc    1260
```

```
ggcgacatcg cctactggga cgaggacgag cacttcttca tcgtggaccg gctgaagagc    1320
ctgatcaaat acaagggcta ccaggtagcc ccagccgaac tggagagcat cctgctgcaa    1380 cacccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg gtggtgttgt gttcgtggac    1560
gaggtgccta aaggactgac cggcaagttg gacgcccgca agatccgcga gattctcatt    1620
aaggccaaga agggcggcaa gatcgccgtg taa                                 1653

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cgggatccga ccatggaaga tgccaaaaac                                     30

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
ggaattctta cacggcgatc ttgcc                                          25

<210> SEQ ID NO 11
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is mixture of a, g, c, and t

<400> SEQUENCE: 11
ggcctgacag aaacaaccnn ngccattctg atcaccccc                           39
```